United States Patent [19]

Chodnekar et al.

[11] 4,002,647
[45] Jan. 11, 1977

[54] NOVEL BENZOFURANYL PEST RETARDANTS

[75] Inventors: Madhukar Subraya Chodnekar, Seltisberg; Peter Loeliger, Munchenstein; Albert Pfiffner, Bulach; Ulrich Schwieter, Reinach; Milos Suchy; Rene Zurfluh, both of Pfaffhausen, all of Switzerland

[73] Assignee: Hoffmann-La Roche Inc., Nutley, N.J.

[22] Filed: May 21, 1975

[21] Appl. No.: 579,358

Related U.S. Application Data

[62] Division of Ser. No. 351,215, April 16, 1973, Pat. No. 3,910,897.

[52] U.S. Cl. .................................... 260/346.2 R
[51] Int. Cl.² ...................................... C07D 307/83
[58] Field of Search ............... 260/240 H, 346.2 R

[56] References Cited

UNITED STATES PATENTS

| | | | |
|---|---|---|---|
| 3,563,982 | 2/1971 | Bowers | 260/240 H |
| 3,749,736 | 7/1973 | Diekman | 260/240 H |

FOREIGN PATENTS OR APPLICATIONS

| | | | |
|---|---|---|---|
| 2,056,590 | 5/1971 | Germany | 260/348 |

OTHER PUBLICATIONS

Bowers, Science, vol. 164, pp. 323 to 325 (1969).

*Primary Examiner*—John D. Randolph
*Attorney, Agent, or Firm*—Samuel L. Welt; Bernard S. Leon; William H. Epstein

[57] ABSTRACT

Alkyl ethers of 2,3-dihydrobenzofuran where the alkyl chain may contain branched chains, unsaturated bonds, epoxy bridges, and may be substituted with halo, alkoxy, lower alkenyloxy, or lower alkynyloxy substituents useful in killing and preventing the proliferation of insects and other pests by upsetting their hormone balance.

41 Claims, No Drawings

NOVEL BENZOFURANYL PEST RETARDANTS

This is a division of application Ser. No. 351,215 filed Apr. 16, 1973, now U.S. Pat. No. 3,910,897 granted Oct. 7, 1975.

SUMMARY OF THE INVENTION

In accordance with this invention, it has been found that compounds of the formula:

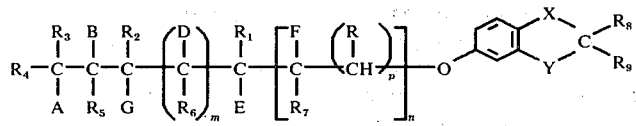

wherein R, $R_1$, $R_2$, $R_5$, $R_6$, $R_7$, $R_8$ and $R_9$ are independently hydrogen or lower alkyl; $R_3$ and $R_4$ are independently lower alkyl; A is individually hydrogen, lower alkyl, lower alkoxy, lower alkenyloxy or lower alkynyloxy; B is individually hydrogen or when A is hydrogen or lower alkyl, B is hydrogen or lower alkoxy, or A and B taken together form a carbon to carbon bond or an oxygen bridge; G and D are individually hydrogen or taken together form a carbon to carbon bond; E and F are individually hydrogen, or taken together form a carbon to carbon bond or, when G and D are hydrogen, E and F are hydrogen or form a carbon to carbon bond or an oxygen bridge; p is an integer from 1 to 2; n and m are independently an integer from 0 to 1; and one of X and Y is oxygen and the other is

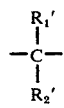

and $R_1'$ are individually hydrogen or lower alkyl; are useful in upsetting the hormone balance of pests such as insects to prevent them from growing and reproducing. The compounds of formula I can be utilized in pesticide compositions which can be applied to various locus to keep them free from pests.

In accordance with this invention the compounds of formula I are produced by the following procedures:

a. reacting a compound of the formula:

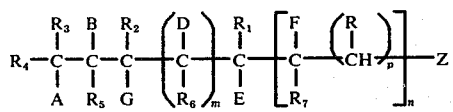

wherein R, $R_1$, $R_2$, $R_3$, $R_4$, $R_5$, $R_6$, $R_7$, A, B, G, D, E, F, p, n and m are as above; and Z is chlorine, bromine, iodine, methylsulphonyloxy or p-toluene-sulphonyloxy with a compound of the general formula

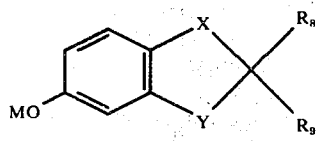

wherein $R_8$, $R_9$, X and Y are as above; and M is alkali metal or alkaline earth metal;

or b. hydrogenating a phenyl derivative of formula I wherein at least one of the pairs of symbols A and B, C and D or E and F taken together form a carbon to carbon bond;

or c. epoxidizing a phenyl derivative of formula I wherein at least one of the pairs of symbols A and B or E and F taken together form a carbon to carbon bond;

or d. reacting a phenyl derivative of formula I wherein at least A and B taken together form a carbon to carbon bond with water or a lower alkanol in the presence of acid or a mercury salt (an organomercury compound obtained being subsequently reduced) and reacting the resulting hydroxy compound with a compound of the general formula $$R_{10}\text{-Z} \qquad \qquad IV$$

wherein $R_{10}$ is lower alkyl, lower alkenyl or lower alkynyl; and Z is as above.

DETAILED DESCRIPTION OF THE INVENTION

The term "halogen" as used throughout this application, includes all four halogens, i.e., bromine, chlorine, fluorine and iodine. As used throughout this application, the term "lower alkyl" comprehends both straight and branched chain saturated hydrocarbon groups containing from 1 to 6 carbon atoms, such as methyl, ethyl, propyl, isopropyl, etc. The term "lower alkoxy" comprehends lower alkoxy groups containing from 1 to 6 carbon atoms such as methoxy, propoxy, ethoxy, etc.

The term "lower alkenyl" designates both straight and branched chain hydrocarbon groups containing an olefinic unsaturation and having from 2 to 6 carbon atoms such as vinyl, allyl, butenyl, pentenyl, etc. The term "lower alkenyloxy" designates an —O—lower alkenyl group where lower alkenyl is as described above. Among the preferred lower alkenyloxy groups are vinyloxy, allyloxy, butenyloxy, etc. The term "lower alkynyl" designates both straight and branched chain hydrocarbon groups having from 2 to 6 carbon atoms and containing an acetylenic unsaturation such as ethynyl, propargyl, butynyl, etc. The term "lower alkynyloxy" designates a —O—lower alkynyloxy group where lower alkynyloxy is as described above. Among the preferred lower alkynyloxy groups are propargyloxy, ethynyloxy and butynyloxy.

The term "alkali metal" designates the metals of the first main group of the periodic chart, e.g., lithium, sodium, potassium, etc. The term "alkaline earth metal" designates metals of the second main group of the periodic chart, i.e., calcium, magnesium, etc.

The compounds of formula I are suitable for combatting pests. In contrast to most of the known pesticides which kill, cripple or drive away the pests, such as contact-poisons and feed-poisons, the compounds of formula I interfere with the hormonal system of the pest organism. In insects, for example, the transformation to the imago, the laying of viable eggs and the development of laid normal eggs is disturbed. The sequence of generations is interrupted and the animals are indirectly killed. The compounds of formula I are also practically non-poisonous to vertebrate animals, the toxicity of these compounds being over 1000 mg/kg body weight. Furthermore, these new compounds are readily degraded. The risk of accumulation is therefore excluded. Therefore, these compounds can be unhesitatingly employed for combatting pests in animals, plants and provisions.

The compounds of formula I are especially suitable for combatting invertebrate animals such as arthropods and nematodes, and particularly Acarina, Orthoptera, Blattidae, Psocoids, Thysanopteroids, Hemiptera, Hymenoptera, Choleoptera, Diptera, Lepidoptera and Neuroptera. Examples of such invertebrate animals are:

| | |
|---|---|
| Metatetranychus | (red citrus spider mite) |
| Tetranychus spp. | (common spider mite) |
| Anthonomus grandis | (boll weevil) |
| Chilo suppressalis | (asiatic rice-borer) |
| Diatraea saccharalis | |
| Heliothis spp. | (bollworm) |
| Pyrausta nubilalis | (corn borer) |
| Carpocapsa pomonella | (codlin moth) |
| Ceratitis capitata | (mediterranean fruit fly) |
| Aonidiella aurantii | (red california scale louse) |
| Aphis gossypii | (cotton aphid) |
| Myzur persicae | (peach aphid) |
| Locusta nigratoria | (migratory locust) |
| Trobolium spp. | (rice flour beetle) |
| Sitophilus spp. | (grain weevil) |
| Ephestia kuhniella | (flour moth) |
| Plodia interpunctella | (dried-fruit moth) |
| Aedes spp. | (mosquitoes) |
| Anopheles spp. | (malarial mosquito) |
| Musca domestica | (house fly) |
| Stomoxys calcitrans | (stable fly [calf-biter]) |
| Blattella germanica | (cockroach) |
| Cochliomyia hominivorax | (screw worm) |

In general, applying a concentration of the compound of formula I as the active substance in an amount of from about $10^{-3}$ to $10^{-6}$ g/cm$^2$ on the locus or material to be protected, i.e., foodstuffs, feeds, textiles, plants, suffices to ensure the desired effect of rendering the material or locus free from pests. Generally, it is preferred to utilize the compounds of formula I above in combination with a suitable inert carrier. Any conventional inert carrier can be utilized.

The compound of formula I can, for example, be used as pesticides in the form of concentrates or granulates or together with carriers in the form of emulsions, suspensions, dusting agents, solutions or aerosols. In special cases, the materials to be protected (e.g., foodstuffs, seeds, textiles, and the like) can also be directly impregnated with the appropriate compound or with a solution thereof. Moreover, the compounds can also be used in a form which only releases them by the action of external influences (e.g., contact with moisture) or in the animal body itself.

The compound of formula I above can be used as solutions suitable for spraying on the material to be protected which can be prepared by dissolving or dispersing these compounds in a solvent such as mineral oil fractions; cold tar oils, oils of vegetable or animal origins; hydrocarbons such as naphthalenes; ketones such as methyl ethyl ketone; or chlorinated hydrocarbons such as tetrachloroethylene, tetrachlorobenzene, and the like. The compounds of formula I above can also be prepared in forms suitable for dilution with water to form aqueous liquids such as, for example, emulsion concentrates, pastes or powders. The compounds of formula I above can be combined with solid carriers for making dusting or strewing powders as, for example, chalk, talc, kaolin, bentonite, diatomaceous earth, fullers earth, lime, calcium carbonate, calcium phosphate, powder and dust for organic waste products. The compositions containing the compound of formula I above can contain, if desired, emulsifiers, dispersing agents, wetting agents, or other active substances such as fungicides, bacteriacides, nematocides, fertilizers and the like. These materials which are to be protected act as bait for the insect. In this manner, the insect, by contacting the material or by contacting the material such as a food impregnated with the compound of formula I above, also contacts or intakes the compound of formula I above.

In general, the pesticide compositions can be formulated according to the procedures described, for example, in Farm Chemicals, Volume 128, page 52 and in the present specification. The pesticide compositions can also contain other additives such as emulsifiers or masking agents.

The pesticide compositions can be made up in the form of concentrates which are suitable for storage and transport. Such concentrates can contain, for example, from about 40% to 80% by weight of a phenyl derivative of formula I. These concentrates can be diluted with the same or different carriers to provide concentrations which are suitable for practical use. In a ready-for-use pesticide composition (e.g., one to be sprayed), concentrations of 0.01–0.5% preferably 0.1%, by weight of a phenyl derivative of formula I can, for example, be present. The concentration can, however, also be smaller or larger.

It will be appreciated from the foregoing that the invention also includes within its scope an agent useful for the control of pests which contains as an essential active ingredient or essential active ingredients one or more of the phenyl derivatives of formula I in association with a compatible carrier material. In addition, the invention includes within its scope a method of rendering a locus subject to or subjected to attack by pests immune to or free from such attack, said method comprising applying to said locus an agent as hereinbefore defined or one or more of the phenyl derivatives of formula I.

Preferred phenyl derivatives of formula I are those in which Y represents an oxygen atom and X represents a methylene group. Especially preferred are phenyl derivatives of formula I in which Y represents an oxygen atom, X represents a methylene group and $R_8$ and $R_9$ each represent a hydrogen atom or $R_8$ represents a methyl group and $R_9$ represents a hydrogen atom or $R_8$ and $R_9$ each represent a methyl group. Other especially preferred phenyl derivatives of formula I are those in which Y represents an oxygen atom, X represents a methylene group which is monosubstituted with a methyl group and $R_8$ and $R_9$ each represent a hydrogen atom and those in which Y represents an oxygen atom, X represents a methylene group, G and D each represent a hydrogen atom, E and F together represent an additional bond, R, $R_2$, $R_5$, $R_6$ and $R_7$ each represent a hydrogen atom and $m$, $n$ and $p$ each stands for 1.

Particularly preferred phenyl derivatives of formula I are:

6-[(6,7-Epoxy-3,7-dimethyl-2-octenyl)-oxy]-2,3-dihydrobenzofuran;

6-[(6,7-Epoxy-3,7-dimethyl-2-octenyl)-oxy]-2-methyl-2,3-dihydrobenzofuran;

6-[(6,7-Epoxy-3,7-dimethyl-2-octenyl)-oxy]-3-methyl-2,3-dihydrobenzofuran;

6-[(6,7-Epoxy-3,7-dimethyl-2-octenyl)-oxy]-2,2-dimethyl-2,3-dihydrobenzofuran;

6-[(6,7-Epoxy-3,7-dimethyl-2-octenyl)-oxy]-3,3-dimethyl-2,3-dihydrobenzofuran;

6-[(6,7-Epoxy-3,7-dimethyl-2-nonenyl)-oxy]-2,3-dihydrobenzofuran;

6-[(6,7-Epoxy-3,7-dimethyl-2-nonenyl)-oxy]-2-methyl-2,3-dihydrobenzofuran;

6-[(6,7-Epoxy-3,7-dimethyl-2-nonenyl)-oxy]-3-methyl-2,3-dihydrobenzofuran;

6-[(6,7-Epoxy-3,7-dimethyl-2-nonenyl)-oxy]-2,2-dimethyl-2,3-dihydrobenzofuran;

6-[(6,7-Epoxy-3,7-dimethyl-2-nonenyl)-oxy]-3,3-dimethyl-2,3-dihydrobenzofuran;

6-[(6,7-Epoxy-3,6,7-trimethyl-2-octenyl)-oxy]-2,3-dihydrobenzofuran;

6-[(6,7-Epoxy-3,6,7-trimethyl-2-octenyl)-oxy]-2-methyl-2,3-dihydrobenzofuran;

6-[(6,7-Epoxy-3,6,7-trimethyl-2-octenyl)-oxy]-3-methyl-2,3-dihydrobenzofuran;

6-[(6,7-Epoxy-3,6,7-trimethyl-2-octenyl)-oxy]-2,2-dimethyl-2,3-dihydrobenzofuran;

6-[(6,7-Epoxy-3,6,7-trimethyl-2)octenyl)-oxy]-3,3-dimethyl-2,3-dihydrobenzofuran;

6-[(6,7-Epoxy-3-ethyl-7-methyl-2-nonenyl)-oxy]-2,3-dihydrobenzofuran;

6-[(6,7-Epoxy-3-ethyl-7-methyl-2-nonenyl)-oxy]-2-methyl-2,3-dihydrobenzofuran;

6-[(6,7-Epoxy-3-ethyl-7-methyl-2-nonenyl)-oxy]-3-methyl-2,3-dihydrobenzofuran;

6-[(6,7-Epoxy-3-ethyl-7-methyl-2nonenyl)-oxy]-2,2-dimethyl-2,3-dihydrobenzofuran;

6-[(6,7-Epoxy-3-ethyl-7-methyl-2-nonenyl)-oxy]-3,3-dimethyl-2,3-dihydrobenzofuran;

6-[(3,6,7-Trimethyl-2,6-octadienyl)-oxy]-2,3-dihydrobenzofuran;

6-[(3,6,7-Trimethyl-2,6-octadienyl)-oxy]-2-methyl-2,3-dihydrobenzofuran;

6-[(3,6,7-Trimethyl-2,6-octadienyl)-oxy]-3-methyl-2,3-dihydrobenzofuran;

6-[(3,6,7-Trimethyl-2,6-octadienyl)-oxy]-2,2-dimethyl-2,3-dihydrobenzofuran;

6-[(3,6,7-Trimethyl-2,6-octadienyl)-oxy]-3,3-dimethyl-2,3-dihydrobenzofuran;

6-[(5-Methoxy-1,5-dimethylheptyl)-oxy]-2,3-dihydrobenzofuran;

6-[(5-Methoxy-1,5-dimethylheptyl)-oxy]-2-methyl-2,3-dihydrobenzofuran;

6-[(5-Methoxy-1,5-dimethylheptyl)-oxy]-2,2-dimethyl-2,3-dihydrobenzofuran;

6-[(5-Methoxy-1,5-dimethylheptyl)-oxy]-3-methyl-2,3-dihydrobenzofuran

6-[(5-Methoxy-1,5-dimethylheptyl)-oxy]-3,3-dimethyl-2,3-dihydrobenzofuran; 6-[(3,7-Dimethyl-7-methoxy-2-nonenyl)-oxy]-2,3-dihydrobenzofuran;

6-[(3,7-Dimethyl-7-methoxy-2-nonenyl)-oxy]-2-methyl-2,3-dihydrobenzofuran;

6-[(3,7-Dimethyl-7-methoxy-2-nonenyl)-oxy]-2,2-dimethyl-2,3-dihydrobenzofuran;

6-[(3,7-Dimethyl-7-methoxy-2-nonenyl)-oxy]-3-methyl-2,3-dihydrobenzofuran;

6-[(3,7-Dimethyl-7-methoxy-2-nonenyl)-oxy]-3,3-dimethyl-2,3-dihydrobenzofuran;

6-[(7-Ethoxy-3,7-dimethyl-2,4-octadienyl)-oxy]-2,3dihydrobenzofuran;

6-[(7-Ethoxy-3,7-dimethyl-2,4-octadienyl)-oxy]-2-methyl-2,3-dihydrobenzofuran;

6-[(7-Ethoxy-3,7-dimethyl-2,4-octadienyl)-oxy]-3-methyl-2,3-dihydrobenzofuran;

6-[(7-Ethoxy-3,7-dimethyl-2,4-octadienyl)-oxy]-2,2-dimethyl-2,3-dihydrobenzofuran;

6-[(7-Ethoxy-3,7-dimethyl-2,4-octadienyl)-oxy]-3,3-dimethyl-2,3-dihydrobenzofuran;

6-[(5-Ethoxy-1,5-dimethylhexyl)-oxy]-2,3-dihydrobenzofuran;

6-[(5-Ethoxy-1,5-dimethylhexyl)-oxy]-2-methyl-2,3-dihydrobenzofuran;

6-[(5-Ethoxy-1,5-dimethylhexyl)-oxy]-3-methyl-2,3-dihydrobenzofuran;

6-[(5-Ethoxy-1,5-dimethylhexyl)-oxy]-2,2-dimethyl-2,3-dihydrobenzofuran;

6-[(5-Ethoxy-1,5-dimethylhexyl)-oxy]-3-3,dimethyl-2,3-dihydrobenzofuran;

6-[(7-Ethoxy-3,7-dimethyl-2-octenyl)-oxy]-2,3-dihydrobenzofuran; 6-[(7-Ethoxy-3,7-dimethyl-2-octenyl)-oxy-2-methyl-2,3-dihydrobenzofuran;

6-[(7-Ethoxy-3,7-dimethyl-2-octenyl)-oxy]-3-methyl-2,3-dihydrobenzofuran;

6-[(7-Ethoxy-3,7-dimethyl-2-octenyl)-oxy]-2,2-dimethyl-2,3-dihydrobenzofuran;

6-[(7-Ethoxy-3,7-dimethyl-2-octenyl)-oxy]-3,3-dimethyl-2,3-dihydrobenzofuran;

6-[(1,3,5-Trimethylhexyl)-oxy]-2,3-dihydrobenzofuran;

6-[(1,3,5-Trimethylhexyl)-oxy]-2-methyl,3-dihydrobenzofuran;

6-[(1,3,5-Trimethylhexyl)-oxy]-3-methyl-2,3-dihydrobenzofuran;

6-[(1,3,5-Trimethylhexyl)-oxy]-2,2-dimethyl-2,3-dihydrobenzofuran;

6-[(1,3,5-Trimethylhexyl)-oxy]-3,3-dimethyl-2,3-dihydrobenzofuran;

6-[(1,3,5,5-Tetramethylhexyl)-oxy]-2,3-dihydrobenzofuran;

6-[(1,3,5,5-Tetramethylhexyl)-oxy]-2-methyl-2,3-dihydrobenzofuran;

6-[(1,3,5,5-Tetramethylhexyl)-oxy]-3-methyl-2,3-dihydrobenzofuran;

6-[(1,3,5,5-Tetramethylhexyl)-oxy]-2,2-dimethyl-2,3-dihydrobenzofuran;

6-[(1,3,5,5-Tetramethylhexyl)-oxy]-3,3-dimethyl-2,3-dihydrobenzofuran;

6-[(1,5,5-Trimethylhexyl)-oxy]-2,3-dihydrobenzofuran;

6-[(1,5,5-Trimethylhexyl)-oxy]-2-methyl-2,3-dihydrobenzofuran;

6-[(1,5,5-Trimethylhexyl)oxy]-3methyl-2,3-dihydrobenzofuran; 6-[(1,5,5-Trimethylhexyl)-oxy]-2,2-dimethyl-2,3-dihydrobenzofuran;

6-[(1,5,5-Trimethylhexyl)-oxy]-3,3-dimethyl-2,3-dihydrobenzofuran;

6-[(3,7,7-Trimethyl-2-octenyl)-oxy]-2,3-dihydrobenzofuran;

6-[(3,7,7-Trimethyl-2-octenyl)-oxy]-2-methyl-2,3dihydrobenzofuran;

6-[(3,7,7-Trimethyl-2-octenyl)-oxy]-3-methyl-2,3-dihydrobenzofuran;

6-[(3,7,7-Trimethyl-2-octenyl)-oxy]-2,2-dimethyl-2,3-dihydrobenzofuran;

6-[(3,7,7-Trimethyl-2-octenyl)-oxy]-3,3-dimethyl-2,3-dihydrobenzofuran;
6-[(3,7,7-Trimethyl-2,4-octadienyl)-oxy]-2,3-dihydrobenzofuran;
6-[(3,7,7-Trimethyl-2,4-octadienyl)-oxy]-2-methyl-2,3-dihydrobenzofuran;
6-[(3,7,7-Trimethyl-2,4-octadienyl)-oxy]-3-methyl-2,3-dihydrobenzofuran;
6-[(3,7,7-Trimethyl-2,4-octadienyl)-oxy]-2,2-dimethyl-2,3-dihydrobenzofuran;
6-[(3,7,7-Trimethyl-2,4-octadienyl)-oxy]-3,3-dimethyl-2,3-dihydrobenzofuran;
6-[(6-Ethoxy-3,6-dimethyl-2-heptenyl)-oxy]-2,3-dihydrobenzofuran;
6-[(6-Ethoxy-3,6-dimethyl-2-heptenyl)-oxy]-2-methyl-2,3-dihydrobenzofuran;
6-[(6-Ethoxy-3,6-dimethyl-2-heptenyl)-oxy]-3-methyl-2,3-dihydrobenzofuran;
6-[(6-Ethoxy-3,6dimethyl-2-heptenyl)-oxy]-2,2-dimethyl-2,3-dihydrobenzofuran;
6-[(6-Ethoxy-3,6-dimethyl-2-heptenyl)-oxy]-3,3-dimethyl-2, 3-dihydrobenzofuran;
6-[(7,8-Epoxy-4,8-dimethyl-3-undecenyl)-oxy]-2,3-dihydrobenzofuran;
6-[(7,8-Epoxy-4,8-dimethyl-3-undecenyl)-oxy]-2-methyl-2, 3-dihydrobenzofuran;
6-[(7,8-Epoxy-4,8-dimethyl-3-undecenyl)-oxy]-3-methyl-2, 3-dihydrobenzofuran;
6-[(7,8-Epoxy-4,8-dimethyl-3-undecenyl)-oxy]-2,2-dimethyl-2, 3-dihydrobenzofuran;
6-[(7,8-Epoxy-4,8-dimethyl-3-undecenyl)-oxy]-3,3-dimethyl-2, 3-dihydrobenzofuran;
6-[(7-Ethoxy-4,7-dimethyl-3-octenyl)-oxy]-2,3-dihydrobenzofuran;
6-[(7-Ethoxy-4,7-dimethyl-3-octenyl)-oxy]-2-methyl-2,3-dihydrobenzofuran;
6-[(7-Ethoxy-4,7-dimethyl-3-octenyl)-oxy]-3-methyl-2,3-dihydrobenzofuran;
6-[(7-Ethoxy-4,7-dimethyl-3-octenyl)-oxy]-2,2-dimethyl-2, 3-dihydrobenzofuran;
6-[(7-Ethoxy-4,7-dimethyl-3-octenyl)-oxy]-3,3-dimethyl-2, 3-dihydrobenzofuran;
6-[(7-Methoxy-1,3,7-trimethyloctyl)-oxy]-2,3-dihydrobenzofuran;
6-[(7-Methoxy-1,3,7-trimethyloxtyl)-oxy]-2-methyl-2,3-dihydrobenzofuran;
6-[(7-Methoxy-1,3,7-trimethyloctyl)-oxy]-3-methyl-2, 3-dihydrobenzofuran;
6-[(7-Methoxy-1,3,7-trimethyloctyl)-oxy]-2,2-dimethyl-2, 3-dihydrobenzofuran;
6-[(7-Methoxy-1,3,7-trimethyloctyl)-oxy]-3,3-dimethyl-2, 3-dihydrobenzofuran;
6-[(3,7-Dimethyl-2-octenyl)-oxy]-2,3-dihydrobenzofuran;
6-[(3,7-Dimethyl-2-octenyl)-oxy]-2-methyl-2,3-dihydrobenzofuran;
6-[(3,7-Dimethyl-2-octenyl)-oxy]-3-methyl-2,3-dihydrobenzofuran;
6-[(3,7-Dimethyl-2-octenyl)-oxy]-2,2-dimethyl-2,3-dihydrobenzofuran;
6-[(3,7-Dimethyl-2-octenyl)-oxy]-3,3-dimethyl-2,3-dihydrobenzofuran;
6-[(6,7-Epoxy-7-ethyl-3-methyl-2-nonenyl)-oxy]-2,3-dihydrobenzofuran;
6-[(6,7-Epoxy-7-ethyl-3-methyl-2-nonenyl)-oxy]-2-methyl-2, 3-dihydrobenzofuran;
6-[(6,7-Epoxy-7-ethyl-3-methyl-2-nonenyl)-oxy]-3-methyl-2, 3-dihydrobenzofuran;
6-[(6,7-Epoxy-7-ethyl-3-methyl-2-nonenyl)-oxy]-2,2-dimethyl-2,3-dihydrobenzofuran;
6-[(6,7-Epoxy-7-ethyl-3-methyl-2-nonenyl)-oxy]-3,3-dimethyl-2,3-dihydrobenzofuran;
6-[(7-Ethyl-7-methoxy-3-methyl-2-nonenyl)-oxy]-2,3-dihydrobenzofuran;
6-[(7-Ethyl-7-methoxy-3-methyl-2-nonenyl)-oxy]-2-methyl-2, 3-dihydrobenzofuran;
6-[(7-Ethyl-7-methoxy-3-methyl-2-nonenyl)-oxy]-3-methyl-2, 3-dihydrobenzofuran;
6-[(7-Ethyl-7-methoxy-3-methyl-2-nonenyl)-oxy]-2,2-dimethyl-2,3-dihydrobenzofuran;
6-[(7-Ethyl-7-methoxy-3-methyl-2-nonenyl)-oxy]-3,3-dimethyl-2,3-dihydrobenzofuran;
6-[(3,7-Dimethyl-7-(2-propynyloxy)-2-octenyl)-oxy]-2,3-dihydrobenzofuran;
6-[(3,7-Dimethyl-7-(2-propynyloxy)-2-oxtenyl)-oxy]-2-methyl-2,3-dihydrobenzofuran;
6-[(3,7-Dimethyl-7-(2-propynyloxy)-2-octenyl)-oxy]-3-methyl-2,3-dihydrobenzofuran;
6-[(3,7-Dimethyl-7-(2-propynyloxy)-2-octenyl)-oxy]-2,2-dimethyl-2,3-dihydrobenzofuran;
6-[(3,7-Dimethyl-7-(2-propynyloxy)-2-octenyl)-oxy]-3,3-dimethyl-2,3-dihydrobenzofuran;
6-[(1,5,5-Trimethyl-2-hexenyl)-oxy]-2,3-dihydrobenzofuran;
6-[(1,5,5-Trimethyl-2-hexenyl)-oxy]-2-methyl-2,3-dihydrobenzofuran;
6-[(1,5,5-Trimethyl-2-hexenyl)-oxy]-3-methyl-2,3-dihydrobenzofuran;
6-[(1,5,5-Trimethyl-2-hexenyl)-oxy]-2,2-dimethyl-2,3-dihydrobenzofuran;
6-[(1,5,5-Trimethyl-2-hexenyl)-oxy]-3,3-dimethyl-2,3-dihydrobenzofuran;
6-[(7-Methoxy-3,7-dimethyloctyl)-oxy]-2,3-dihydrobenzofuran;
6-[(7-Methoxy-3,7-dimethyloctyl)-oxy]-2-methyl-2,3-dihydrobenzofuran;
6-[(7-Methoxy-3,7-dimethyloctyl)-oxy]-3-methyl-2,3-dihydrobenzofuran;
6-[(7-Methoxy-3,7-dimethyloctyl)-oxy]-2,2-dimethyl-2,3-dihydrobenzofuran;
6-[(7-Methoxy-3,7-dimethoyloctyl)-oxy]-3,3-dimethyl-2,3-dihydrobenzofuran;
6-[(3,7-Dimethyl-6-methoxy-2-octenyl)-oxy]-2,3-dihydrobenzofuran;
6-[(3,7-Dimethyl-6-methoxy-2-octenyl)-oxy]-2-methyl-2,3-dihydrobenzofuran;
6-[(3,7-Dimethyl-6-methoxy-2-octenyl)-oxy]-3-methyl-2,3-dihydrobenzofuran;
6-[(3,7-Dimethyl-6-methoxy-2-octenyl)-oxy]-2,2-dimethyl-2,3-dihydrobenzofuran;
6-[(3,7-Dimethyl-6-methoxy-2-oxtenyl)-oxy]-3,3-dimethyl-2,3-dihydrobenzofuran;
6-[(6-Methoxy-3,7,7-trimethyl-2-octenyl)-oxy]-2,3-dihydrobenzofuran;
6-[(6-Methoxy-3,7,7-trimethyl-2-octenyl)-oxy]-2-methyl-2,3-dihydrobenzofuran;
6-[(6-Methoxy-3,7,7-trimethyl-2-octenyl)-oxy]-3-methyl-2,3-dihydrobenzofuran;
6-[(6-Methoxy-3,7,7-trimethyl-2-oxtenyl)-oxy]-2,2-dimethyl-2,3-dihydrobenzofuran; and
6-[(6-Methoxy-3,7,7-trimethyl-2-octenyl)-oxy]-3,3-dimethyl-2,3-dihydrobenzofuran.

The compounds of formula I when they contain double bonds or oxygen bridges can exist as cis or trans isomers or as mixtures of cis and trans isomers about each of these bridges or double bonds.

According to embodiment (a) of the present process, a compound of formula II is reacted with a compound of formula III.

Preferred starting materials of formula II are:
1-Bromo-3,7-dimethyl-2,6-nonadiene;
1-Bromo-3,6,7-trimethyl-2,6-octadiene;
1-Bromo-3-ethyl-7-methyl-2,6-nonadiene;
1,5-Dimethyl-5-methoxy-heptyl p-toluenesulphonate;
1-Bromo-3,7-dimethyl-7-methoxy-2-nonene;
1-Bromo-3,7-dimethyl-7-ethoxy-2,4-octadiene;
5-Ethoxy-1,5-dimethylhexyl p-toluenesulphonate;
7-Ethoxy-1-bromo-3,7-dimethyl-2-octene;
1,3,5-Trimethylhexyl p-toluenesulphonate;
1,3,5,5-Tetramethylhexyl p-toluenesulphonate;
1,5,5-Trimethylhexyl p-toluenesulphonate;
1-Bromo-3,7,7-trimethyl-2-octene;
1-Bromo-3,7,7-trimethyl-2,4-octadiene;
6-Ethoxy-1-bromo-3,6-dimethyl-2-heptene;
1-Bromo-4,8-dimethyl-3,7-undecadiene;
7-Ethoxy-1-bromo-4,7-dimethyl-3-octene;
7-Methoxy-1,3,7-trimethyloctyl p-toluenesulphonate;
1-Bromo-3,7-dimethyl-2-octene;
7-Ethyl-1-bromo-3-methyl-2,6-nonadiene;
7-Ethyl-1-bromo-7-methoxy-3-methyl-2-nonene;
1-Bromo-3,7-dimethyl-7-propynyloxy-2-octene;
2-Bromo-6,6-dimethyl-3-heptene;
3,7-Dimethyl-7-methoxy-octyl p-toluenesulphonate;
1-Bromo-3,7-dimethyl-6-methoxy-2-octene; and
1-Bromo-6-methoxy-3,7,7-trimethyl-2-octene.

Preferred starting materials of formula III are:
6-Hydroxy-2,3-dihydrobenzofuran;
6-Hydroxy-2-methyl-2,3-dihydrobenzofuran;
6-Hydroxy-3-methyl-2,3-dihydrobenzofuran;
6-Hydroxy-2,2-dimethyl-2,3-dihydrobenzofuran; and
6-Hydroxy-3,3-dimethyl-2,3-dihydrobenzofuran.

The reaction of a phenolate of formula III with a halide or a tosylate of formula II is carried out in an inert organic solvent, preferably in dimethylformamide, dioxane, hexamethylphosphoric acid triamide, tetrahydrofuran or in a combination of two or more of these solvents. The corresponding phenol is expediently used and the reaction carried out in the presence of an alkali metal or alkaline earth metal, preferably in the presence of sodium or a corresponding hydride or amide, preferably sodium hydride of sodium amide. By following this procedure, the corresponding phenolate is formed from the phenol. The reaction temperature is not of critical importance. The reaction can expediently be carried out at a temperature between −20° C. and the boiling point of the reaction mixture. A preferred reaction temperature is room temperature, especially when Z in formula II is bromine.

Phenyl derivatives of formula I in which at least one of the pairs of symbols A and B, G and D or E and F together represent an additional bond can be hydrogenated in accordance with embodiment (b) of the present process using catalytically activated hydrogen in an inert organic solvent (e.g., ethyl acetate or methanol) at a temperature between room temperature and the boiling point of the solvent and at normal or elevated pressure. Suitable catalysts are, for example, Raney nickel or noble metals (e.g., platinum or palladium).

The epoxidation of phenyl derivatives of formula I in which at least one of the pairs of symbols A and B or E and F together represent an additional bond in accordance with embodiment (c) of the present process is expediently carried out by dissolving the phenyl derivative in an inert solvent, especially in a halogenated hydrocarbon such as methylene chloride or chloroform, and treating the solution at a temperature between 0° C. and room temperature with an organic peracid (e.g., perbenzoic acid, m-chloroperbenzoic acid or perphthalic acid) or by suspending the phenyl derivative in water, mixing the suspension with a sufficient quantity of an inert solvent (e.g., dioxane, tetrahydrofuran or 1,2-dimethoxy-ethane) to provide a homogeneous, concentrated solution and introducing N-bromosuccinimide portionwise into this solution at a temperature between 0° C. and room temperature. The resulting bromohydrin can be smoothly converted into the desired epoxide by the action of an alkali metal base, especially sodium methylate in methanol.

In embodiment (d) of the present process a phenyl derivative of formula I in which at least A and B together represent an additional bond is reacted with water or a lower alkanol, preferably methanol or ethanol. This reaction is carried out in the presence of an acid, preferably a mineral acid (e.g., sulfuric acid). As the solvent there is expediently used an inert organic solvent, preferably tetrahydrofuran. The reaction can be carried out at a temperature between 0° C. and the reflux temperature of the reaction mixture, preferably between 0° and 40° C. Phenyl derivatives of formula I in which A represents a hydroxy or lower alkoxy group are obtained. It is especially preferred to carry out embodiment (d) of the process using the procedure described in J. Am. Chem. Soc. 91, 5646 (1969). This procedure consists in reacting such an unsaturated phenyl derivative with water or a lower alkanol and a mercury salt, the mercury-containing intermediate being subsequently reduced without isolation. Suitable mercury salts include mercury acetate and other acylates, mercury nitrate, mercury trifluoroacetate and mercury halides. Suitable reducing agents include the alkali metal borohydrides, hydrazine and sodium amalgam. Where water is added to the terminal double bond of a phenyl derivative of formula I, there is obtained a hydroxy-substituted phenyl derivative of formula I in which A represents a hydroxy group. Such a hydroxy-substituted phenyl derivative is etherified with a compound of formula IV. This etherification is carried out in the same manner as previously described for the reaction of a compound of formula II with a compound of formula III.

The starting materials of formula II are, in part, known. They are prepared by reacting a ketal of the formula:

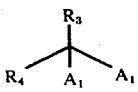
(V)

wherein $R_3$ and $R_4$ are as above; and $A_1$ is lower alkoxy; with a vinyl ether of the formula:

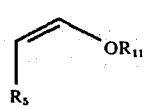
(VI)

wherein $R_5$ is as above; and $R_{11}$ is lower alkyl.

The reaction is carried out in the presence of a Lewis acid such as, for example, boron trifluoride (used in the form of the etherate) or ferric chloride and is advantageously carried out in the absence of a solvent. It is preferred to carry out this reaction at a temperature between 0° C. and room temperature. According to this reaction there is obtained an acetal of the formula:

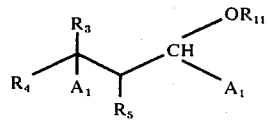 (VII)

wherein $R_3$, $R_4$, $R_5$, $R_{11}$, and $A_1$ are as above.

An acetal of formula VII is subjected to an acid hydrolysis in the usual manner (e.g., using 5% by weight aqueous phosphoric acid). The hydrolysis is expediently carried out with warming at 60° to 100° C. in the presence of a small amount of hydroquinone. There is obtained an aldehyde of the formula:

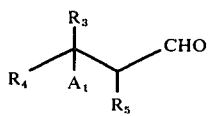 (VIII)

wherein $R_3$, $R_4$, $R_5$ and $A_1$ are as above.

From acetals of formula VII there are obtained alpha,beta-unsaturated aldehydes of the formula:

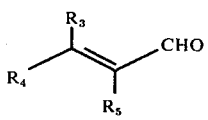 (IX)

wherein $R_3$, $R_4$ and $R_5$ are as above.

The conversion of an acetal of formula VII into an alpha,beta-unsaturated aldehyde of formula IX is carried out by pyrolysis in the presence of an acid catalyst (e.g., p-toluenesulfonic acid or ammonium dihydrogen phosphate) or by warming at 50° to 100° C. in a dilute aqueous mineral acid (e.g., 10% by weight aqueous hydrochloric acid).

Aldehydes of the formula:

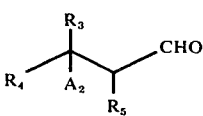 (X)

wherein $A_2$ is lower alkyl; and $R_3$, $R_4$ and $R_5$ are as above; are prepared by reacting an alpha,beta-unsaturated aldehyde of formula IX with a compound of the formula:

 (XI)

wherein X' is chlorine, bromine or iodine; and $A_2$ is as above;
in the presence of cuprous salts (e.g., cuprous chloride) or with an organo-copper complex of the formula:

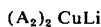 (XII)

wherein $A_2$ is as above; Cu is copper; and Li is lithium. The reaction is carried out in an ether, preferably diethyl ether or tetrahydrofuran, at a temperature between −30° C. and 0° C. The preparation of the organo-copper complex is carried out, for example, as described in J. Org. Chem. 31, 3128 (1966).

Other valuable starting materials are hydroxy-acetals of the formula:

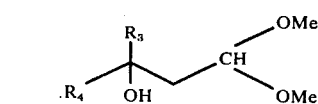 (XIII)

wherein $R_3$ and $R_4$ are as above.

The hydroxyl group in a hydroxy-acetal of formula XIII can be etherified with a lower alkyl halide, lower alkenyl halide or lower alkynyl halide in the same manner as previously described for the reaction of a compound of formula II with a compound of formula III. A hydroxy-acetal of formula XIII is obtained according to the method described in Chem. Abstr. 51, 2854 (1957) from a compound of the formula:

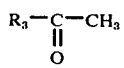 (XIV)

wherein $R_3$ is as above;
by reaction with methyl formate in methanol. A resulting compound of the formula:

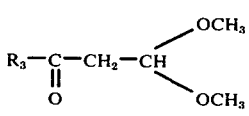 (XV)

wherein $R_3$ is as above;
is reacted in a manner known per se with a compound of the formula:

 (XVI)

wherein $R_4$ is as above.
There is thus obtained, after acid hydrolysis of the acetal function (optionally after etherification of the hydroxyl group), an aldehyde of the formula:

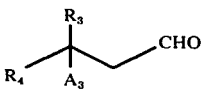 (XVII)

wherein $A_3$ is hydroxy, lower alkoxy, lower alkenyloxy or lower alkynyloxy groups; and $R_3$ and $R_4$ are as above.

The aldehydes of formulae VIII, IX, X and XVII can be generically formulated thus:

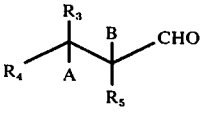 (XVIII)

wherein $R_3$, $R_4$, $R_5$, A and B are as above.

The starting materials of formula II in which R and $R_7$ each represent a hydrogen atom can be prepared from the aldehydes of formula XVIII by means of conventional Wittig, Horner and/or Grignard reactions as well as by conventional enol ether condensation in a manner known per se to produce compounds of the formulae:

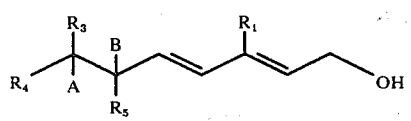  XIX-A;

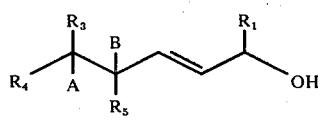  XIX-B;

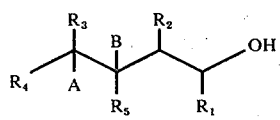  XIX-C;

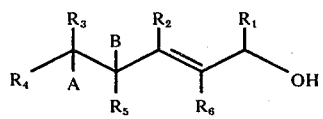  XIX-D;

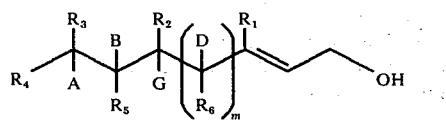  XIX-E wherein $R_1$, $R_2$, $R_3$, $R_4$, $R_5$, $R_6$, A, B, G and D are as above.

The compounds of formula XVIII are converted to the compound of formula XIX-A via the following intermediate:

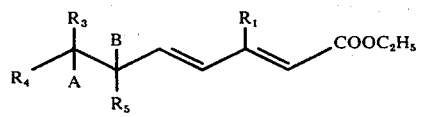  XVIII-A wherein A, B, $R_1$, $R_3$, $R_4$ and $R_5$ are as above.

The compound of formula XVIII-A is prepared by reacting the compound of formula XVIII with a compound of the formula:

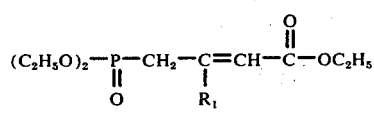

wherein $R_1$ is as above;
via a Horner reaction utilizing conditions conventional in Horner reactions. The compound of formula XVIII-A is converted to the compound of formula XIX-A by reduction with a complex metal hydride such as lithium aluminum hydride.

The compound of formula XVIII is converted to the compound of formula XIX-B by first reacting the compound of formula XVIII with a compound of the formula:

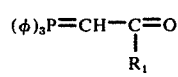

wherein $\phi$ is phenyl and $R_1$ is as above;

via a Wittig reaction to produce a compound of the formula:

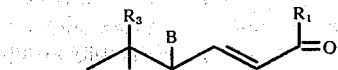  XVIII-B wherein A, B, $R_1$, $R_3$, $R_4$ and $R_5$ are as above.

The compound of formula XVIII-B is then reduced with a complex metal hydride such as lithium aluminum hydride to form the compound of formula XIX-B. Any of the conditions conventional in reduction with a complex metal hydride and Wittig reactions can be used in carrying out this series of reactions.

The compound of formula XIX-C is prepared from the compound of formula XVIII via an intermediate of the formula:

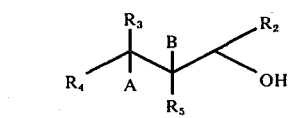  XVIII-C wherein $R_2$, $R_3$, $R_4$, $R_5$, A and B are as above.

The compound of formula XVIII-C is formed by reacting the compound of formula XVIII via a Grignard reaction with a compound of the formula:

wherein $R_2$ and X' are as above.

The hydroxy compound of formula XVIII-C is next converted to the corresponding compound where the hydroxy group is replaced by a halide via halogenation. Any conventional means can be utilized to halogenate the compound of formula XVIII-C. The halide is next converted by conventional means to the corresponding Grignard salt. This Grignard salt can be reacted via a conventional Grignard reaction with a compound of the formula:

wherein $R_1$ is as above;
to form the compound of formula XIX-C.

The compound of formula XVIII-C is converted to the compound of formula XIX-D via an intermediate of the formula

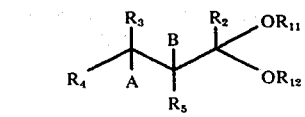  XVIII-D wherein $R_2$, $R_3$, $R_4$, $R_5$, A and B are as above;
and $R_{11}$ and $R_{12}$ are lower alkyl;
and an intermediate of the formula

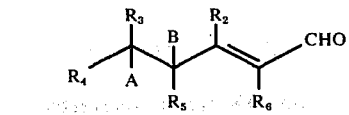  XVIII-Di wherein $R_2$, $R_3$, $R_4$, $R_5$, $R_6$, A and B are as above.

The compound of formula XVIII-D is formed by first oxidizing the hydroxy group in the compound of formula XVIII-C to the corresponding keto group and then ketalizing the keto group with a lower alkanol. Any conventional means of oxidizing a hydroxy group to a keto group such as by treatment with a chromatic oxidizing agent, preferably chromium trioxide, can be utilized to carry out this reaction. The ketalization of this keto group to form the compound of formula XVIII-D can be carried out by conventional procedures. The compound of formula XVIII-D is converted to the compound of formula XVIII-Di by conventional enol ether condensation with a compound of the formula

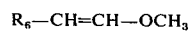

wherein $R_6$ is as above followed by acid hydrolysis. The compound of formula XVIII-Di can be converted to the compound of formula XIX-D by reaction with a compound of the formula

wherein $R_1$ and $X'$ are as above via a conventional Grignard reaction.

The hydroxy compounds of formulae XIX-B, XIX-C and XIX-D can be generically formulated as:

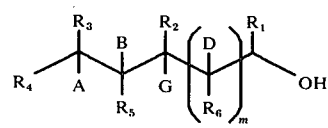

XVIII-E wherein $R_1$, $R_2$, $R_3$, $R_4$, $R_5$, $R_6$, A, B, G and D are as above.

The compound of formula XVIII-E can be converted to the compound of formula XIX-E by first oxidizing the hydroxy group in the compound of formula XVIII-E to an oxo group by conventional means such as by treating with an oxidizing agent such as chromiun trioxide, then reacting this oxo compound via a Horner reaction with a compound of the formula

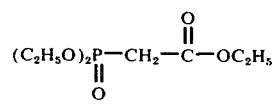

and finally treating this reaction product with a complex metal hydride reducing agent such as lithium aluminum hydride in the manner described hereinbefore.

The compounds of formulae XIX-A, XIX-B, XIX-C, XIX-D and XIX-E can be generically formulated as a compound of the formula

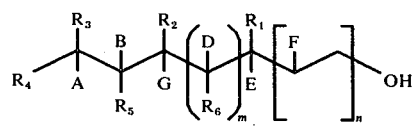

XIX wherein $R^1$, $R^2$, $R^3$, $R^4$, $R^5$, $R^6$, A,B,G,D,E,F, $m$ and $n$ are as above.

The compound of formula XIX can be converted to compounds of formula II by conventional means such as by treating in a manner known per se with thionyl chloride, phosphorous tribromide, etc. to form the desired halide of formula II or by treating with tosyl chloride or mesyl chloride to form the tosylates or mesylates of formula II.

Compounds of the formula

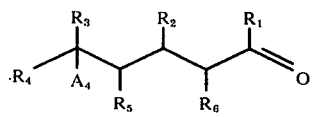

XX wherein $A_4$ is a lower alkoxy or hydroxy; and $R_1$, $R_2$, $R_3$, $R_4$, $R_5$ and $R_6$ are as above
are, in part, known. They are prepared by reacting a compound of the formula

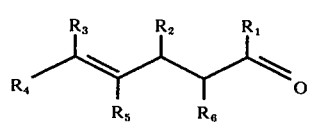

XXI wherein $R_1$, $R_2$, $R_3$, $R_4$, $R_5$ and $R_6$ are as above with a lower alkanol or water in the presence of mineral acid.

Compounds of the formula

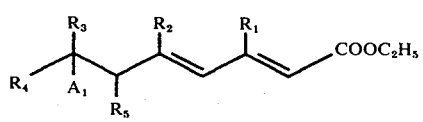

XXII wherein $A_1$ is lower alkoxy; and $R_1$, $R_2$, $R_3$, $R_4$ and $R_5$ are as above are valuable starting materials. They are prepared in a simple manner from compounds of the formula

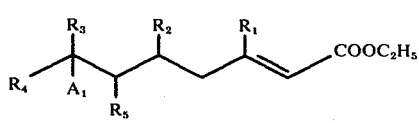

XXIII wherein $A_1$, $R_1$, $R_2$, $R_3$, $R_4$ and $R_5$ are as above by bromination and dehydrobromination according to the method described in J. Org. Chem. 28, 2735 (1963)

Dienones of the formula

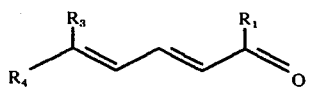

XXIV wherein $R_1$, $R_3$ and $R_4$ are as above are valuable for the preparation of compounds having quaternary carbon atoms. Such dienones are obtained by reacting a compound of the formula

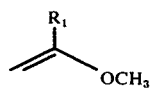

XXV wherein $R_1$ is as above with an acetylenic carbinol of the general formula

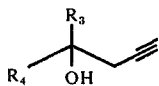 XXVI wherein $R_3$ and $R_4$ are as above.

The reaction of a compound of formula XXV with an acetylenic carbinol of formula XXVI is carried out in an inert organic solvent, preferably a hydrocarbon (e.g., petroleum ether), in the presence of an acid catalyst (e.g., phosphoric acid or p-toluenesulphonic acid) at a temperature between 50° C. and the boiling point of the reaction mixture. The β-keto-allene obtained as the primary product is subjected to a base isomerization under the conditions described in Helv., 50, 1158 (1967) to give the desired conjugated dienone of formula XXIV. From such dienones there are obtained by reaction with organo-copper complexes of formula XII, after isomerization, compounds of the formula

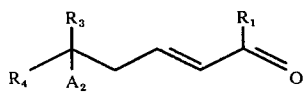 XXVII wherein $R_1$, $R_3$ and $R_4$ are as above; and $A_2$ is a lower alkyl group.

The reaction of a dienone of formula XXIV with an organo-copper complex of formula XII is carried out as previously described for the reaction of an α,β-unsaturated aldehyde of formula IX with an organo-copper complex of formula XII, the primary product being subjected to an acid isomerization (e.g., by means of hydrochloric acid in acetone or tetrahydrofuran) to give a conjugated enone of formula XXVII.

A further lower alkyl group can be introduced into compounds of formula XXVII by reaction with an organo-copper complex of formula XII to give compounds of the formula

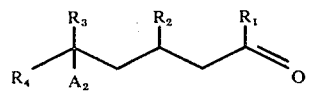 XXVIII wherein $R_1$, $R_2$, $R_3$ and $R_4$ are as above; and $A_2$ is a lower alkyl group.

The hydroxyl group in a compound of the formula

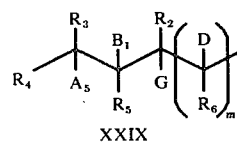
XXIX wherein $R_1$, $R_2$, $R_3$, $R_4$, $R_5$, $R_6$, G, D and m are as above; $A_5$ is hydrogen or lower alkyl; $B_1$ is hydroxy; $A_6$ is hydroxy and $B_2$ is hydrogen
can be etherified with a lower alkyl halide, lower alkenyl halide or lower alkynyl halide in the same manner as described earlier for the reaction of a compound of formula II with a compound of formula III.

Compounds of the formula

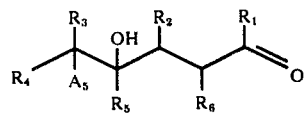 XXXI wherein $R_1$, $R_2$, $R_3$, $R_4$, $R_5$ and $A_5$ are as above are prepared by reacting a compound of the formula

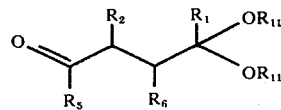 XXXII wherein $R_1$, $R_2$, $R_5$ and $R_6$ are as above and $R_{11}$ is lower alkyl with a Grignard reagent of the formula

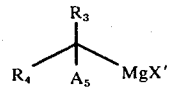 XXXIII wherein X', $A_5$, $R_3$ and $R_4$ are as above followed by liberation of the carbonyl function by treatment with acid.

Compounds of formula XXXII are generally accessible from epoxides of the formula

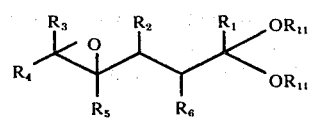 XXXIV wherein $R_1$, $R_2$, $R_3$, $R_4$, $R_5$, $R_6$, and $R_{11}$ are as above. These epoxides are, in turn, prepared from the corresponding olefins in the same manner as previously described for the epoxidation of a phenyl derivative of formula I in which at least one of the pairs of symbols A and B, G and D or E and F together represent an additional bond. If epoxides of formula XXXIV are treated with strong acids in the presence of water (e.g., with hydrochloric acid in tetrahydrofuran/water), there are obtained glycols which yield the desired compounds of formula XXXII upon treatment with lead tetraacetate, sodium periodate, etc.

The compounds of formulae XX, XXVII and XXVIII can be generically formulated thus:

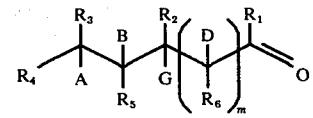 XXXV wherein $R_1$, $R_2$, $R_3$, $R_4$, $R_5$, $R_6$, A, B, G, D and m are as above.

From these compounds there can be prepared by means of simple reactions which are known per se the alcohols corresponding to formula II which have the formulae:

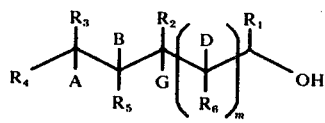

XXXVI-A

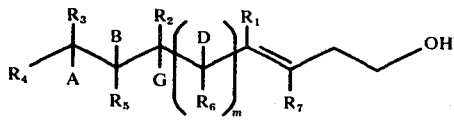

XXXVI-B

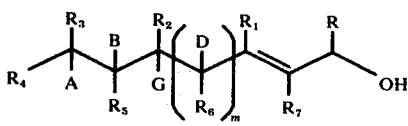

XXXVI-C wherein A, B, G, D, m, R, $R_1$, $R_2$, $R_3$, $R_4$, $R_5$ $R_6$ and $R_7$ are as above.

In these reactions to convert the compound of formula XXXV to the compounds of formulas XXXVI-A, XXXVI-B and XXXVI-C conventional and standard Wittig and Grignard reaction conditions can be used. The reduction reactions are carried out by utilizing a complex metal hydride such as lithium aluminum hydride under conditions conventional and standard for reduction reactions with complex metal hydrides.

The compound of formula XXXVI-A is formed from the compound of formula XXXV by reduction with a complex metal hydride such as lithium aluminum hydride.

In preparing the compound of formula XXXVI-B, the compound of formula XXXV is first reacted via a Wittig reaction with a salt of the formula

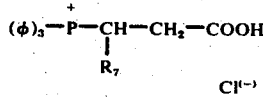

wherein 0 is phenyl and $R_7$ is as above to form an intermediate of the formula

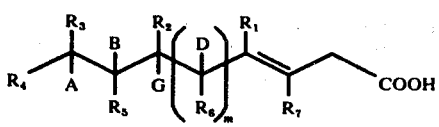

XXXV-B wherein $R_1$, $R_2$, $R_3$, $R_4$, $R_5$, $R_6$, $R_7$, A, B, G, D and m are as above.

The intermediate of the formula XXXV-B is then reduced with a complex metal hydride to form the compound of formula XXXVI-B.

The compound of formula XXXV is converted to the compound of formula XXXVI-C by first reacting the compound of formula XXXV, via a Wittig reaction, with a compound of the formula

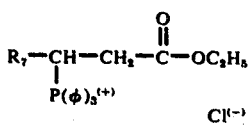

wherein $\phi$ and $R_7$ are as above to form an ester of the formula

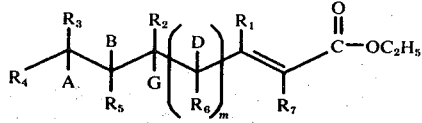

XXXV-C wherein A, B, D, G, $R_1$, $R_2$, $R_3$, $R_4$, $R_5$, $R_6 R_7$ and m are as above.

This ester is then treated with a complex metal hydride to convert the ester group to a hydroxy group and form the corresponding compound of the formula

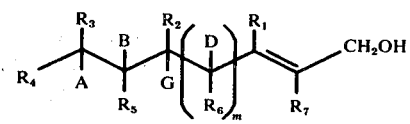

XXXV-Ci wherein $R_1$, $R_2$, $R_3$, $R_4$, $R_5$, $R_6$, $R_7$, m, A, B, G and D are as above.

This hydroxy compound is then oxidized to a compound of the formula

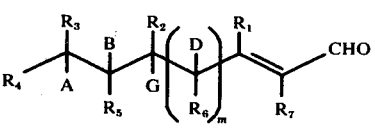

XXXV-Cii wherein $R_1$, $R_2$, $R_3$, $R_4$, $R_5$, $R_6$, $R_7$, m, A, B, G and D are as above.

Any conventional method of oxidizing an alcohol to an aldehyde can be utilized to carry out this oxidation. Among these methods are included treating the compound of formula XXXV-Ci with an oxidizing agent such as manganese dioxide. The compound of formula XXXV-Cii is converted to the compound of formula XXXVI via a Grignard reaction with a compound of the formula R-MgX' wherein R and X' are as above.

Compounds of the formulae XXXVI-A, XXXVI-B and XXXVI-C can be converted to compounds of the formula II in the same manner as described in connection with the conversion of compounds of the formula XIX to compounds of the formula II.

The starting materials of formula III are, for the most part, known compounds.

The 6-hydroxy-2,3-dihydrobenzofurans which are disubstituted in position 2 or 3 can be prepared according to methods known per se as follows:

3-Methoxy-phenol is etherified with 2-methyl-allyl chloride and converted by means of a Claisen rearrangement into 2-hydroxy-4-methoxy-β-methyl-allyl-benzene which can be cyclized in the presence of acid catalysts such as hydrobromic acid/glacial acetic acid or pyridine hydrochloride with simultaneous demethylation to give 2,2-dimethyl-6-hydroxy-2,3-dihydrobenzofuran.

Starting, for example, from 1-(2,4-dimethoxyphenyl)-ethanol and treating same with thionyl chloride there can be obtained 1-(2,4-dimethoxy-phenyl)- ethyl chloride which can be converted by reaction with potassium cyanide and subsequent methylation with sodium amide and methyl iodide into 2-(2,4-dimethoxy-phenyl)-2-methyl-propionitrile. Alkaline hydrolysis of the nitrile group and subsequent reduction of the carboxyl group with lithium aluminum hydride gives 2-(2,4-dimethoxy-phenyl)-2-methyl-propanol which, by treatment with hydrobromic acid/glacial acetic acid and subsequent cyclization of the resulting 2-(2,4-dihydroxy-phenyl)-2-methyl-propyl bromide with potassium carbonate in acetone, yields 3,3-dimethyl-6-hydroxy-2,3-dihydrobenzofuran.

The phenyl derivatives of formula I are obtained, insofar as the side-chain is unsaturated, as cis/trans isomer mixtures. The isomer mixture can be separated into the individual isomers in the usual manner; for example, by fractional distillation or preparative gas chromatography. Further, the starting materials of formula II, insofar as they are present as an isomer mixture, can also be separated into the individual isomers in the usual manner; for example, by fractional distillation or chromatography.

The following examples are illustrative but not limitative of this invention. In these examples the ether utilized is diethyl ether and temperatures are given in ° C. The term half concentrated hydrochloric acid indicates an aqueous solution containing 10% by weight hydrogen chloride. The term semi-saturated sodium chloride solution indicates an aqueous solution containing 15% by weight sodium chloride. The term dilute sulfuric acid indicates an aqueous solution containing 10% by weight sulfuric acid. The term concentrated sulfuric acid indicates an aqueous solution containing 96% by weight sulfuric acid.

EXAMPLE 1

A mixture of 27.7 g. of 6-hydroxy-2,3-dihydrobenzofuran, 52.1 g. of geranyl bromide and 41.4 g. of anhydrous powdered potassium carbonate in 200 ml. of methyl ethyl ketone is heated under reflux with stirring for 70 hours. The cooled reaction mixture is filtered, the residual potassium carbonate washed with acetone and the filtrate evaporated. By chromatography on silica gel with hexane/diethyl ether (4:1 parts by volume) there is obtained pure 6-[(3,7-dimethyl-2,6-octadienyl)-oxy]-2,3-dihydrobenzofuran of boiling poiint 130° C./0.001 mmHg.; $n_D^{20} = 1.5414$.

EXAMPLE 2

By the procedure of Example 1:

1-bromo-3,7-dimethyl-2,6-nonadiene and 6-hydroxy-2,3-dihydrobenzofuran are reacted to form 6-[(3,7-dimethyl-2,6-nonadienyl)-oxy]-2,3-dihydrobenzofuran of boiling point 138° C./0.002 mmHg; $n_D^{20} = 1.5382$;

1-bromo-3,6,7-trimethyl-2,6-octadiene and 6-hydroxy-2,3-dihydrobenzofuran are reacted to form 6-[(3,6,7-trimethyl-2,6-octadienyl)-oxy]-2,3-dihydrobenzofuran of boiling point 124°–126° C./0.001 mmHg; $n_D^{20} = 1.5412$;

1-bromo-3-ethyl-7-methyl-2,6-nonadiene and 6-hydroxy2,3-dihydrobenzofuran are reacted to form 6-[(3-ethyl-7-methyl-2,6-nonadienyl)-oxy]-2,3-dihydrobenzofuran of boiling point 132° C. -134° C./0.001 mmHg; $n_D^{20} = 1.5346$;

1-bromo-3,7-dimethyl-2,6-nonadiene and 6-hydroxy-2-methyl-2,3-dihydrobenzofuran are reacted to form 6-[(3,7-dimethyl-2,6-nonadienyl)-oxy]-2-methyl-2,3-dihydrobenzofuran of boiling point ca. 145° C./0.001 mmHg; $n_D^{20} = 1.5286$;

1-bromo-3,7-dimethyl-2,6-nonadiene and 6-hydroxy-3-methyl-2,3-dihydrobenzofuran are reacted to form 6-[(3,7-dimethyl-2,6-nonadienyl)-oxy]-3-methyl-2,3-dihydrobenzofuran of boiling point 147° C./0.001 mmHg; $n_D^{20} = 1.5312$; and 1-bromo-3,7,9-trimethyl-2,6-decadiene and 6-hydroxy-2,3-dihydrobenzofuran are reacted to form 6-[(3,7,9-trimethyl-2,6-decadienyl)-oxy]-2,3-dihydrobenzofuran of boiling point (bulb-tube) 112° C./0.03 mmHg; $n_D^{20} = 1.5271$.

EXAMPLE 3

18 g. of 6-[(3,7-dimethyl-2,6-octadienyl)-oxy]-2,3-dihydrobenzofuran are dissolved in 180 ml. of methylene chloride and, with stirring and ice cooling at 0°–5° C., 14.3 g. of 80% m-chloroperbenzoic acid are added portionwise. The mixture is then stirred for a further 2 hours with ice cooling. The mixture is subsequently diluted with 360 ml. of diethyl ether and washed successively with ice-cold 1-N aqueous sodium hydroxide and water. The organic phase is dried over sodium sulfate and evaporated. By chromatography on silica gel with hexane/diethyl ether (7:3 parts by volume) there is obtained pure 6-[(6,7-epoxy-3,7-dimethyl-2-octenyl)-oxy]-2,3-dihydrobenzofuran of boiling point ca. 150° C./0.001 mmHg; $n_D^{20} = 1.5346$.

EXAMPLE 4

By the procedure of Example 3:

6-[(3,7-dimethyl-2,6-nonadienyl)-oxy]-2,3-dihydrobenzofuran is converted to 6-[(6,7-epoxy-3,7-dimethyl-2-nonenyl)-oxy]-2,3-dihydrobenzofuran of boiling point ca. 150° C./0.001 mmHg; $n_D^{20} = 1.5324$;

6-[(3,6,7-trimethyl-2,6-octadienyl)-oxy]-2,3-dihydrobenzofuran is converted to 6-[(6,7-epoxy-3,6,7-trimethyl-2-octenyl)-oxy]-2,3-dihydrobenzofuran of boiling point ca. 150° C./0.001 mmHg; melting point 62°–64° C.;

6-[(3-ethyl-7-methyl-2,6-nonadienyl)-oxy]-2,3-dihydrobenzofuran is converted to 6-[(6,7-epoxy-3-ethyl-7-methyl-2-nonenyl)-oxy]-2,3-dihydrobenzofuran of boiling point ca. 150° C./0.001 mmHg; $n_D^{20} = 1.5287$;

6-[(3,7-dimethyl-2,6-nonadienyl)-oxy]-2methyl-2,3-dihydrobenzofuran is converted to 6-[(6,7-epoxy-3,7-dimethyl-2-nonenyl)-oxy]-2-methyl-2,3-dihydrobenzofuran of boiling point ca. 150° C./0.001 mmHg; $n_D^{20} = 1.5286$;

6-[(3,7-dimethyl-2,6-nonadienyl)-oxy]-3-methyl-2,3-dihydrobenzofuran is converted to 6-[(6,7-epoxy-3,7-dimethyl-2-nonenyl)-oxy]-3-methyl-2,3-dihydrobenzofuran of boiling point ca. 160°–165° C./0.001 mmHg; $n_D^{20} = 1.5261$;

6-[(3,7,9-trimethyl-2,6-decadienyl)-oxy]-2,3-dihydrobenzofuran is converted to 6-[(6,7-epoxy-3,7,9-trimethyl-2-decenyl)-oxy]-2,3-dihydrobenzofuran of boiling point (bulb-tube) 140° C./0.03 mmHg; $n_D^{23} = 1.5219$; and 6-[(7-ethyl-3-methyl-2-nonenyl)-oxy]-2,3-dihydrobenzofuran is converted to 6-[(6,7-epoxy-7-ethyl-3-methyl-2-nonenyl)-oxy]-2,3-dihydrobenzofuran; $n_D^{20} = 1.5273$.

EXAMPLE 5

0.87 g. of a 55% by weight sodium hydride dispersion in oil are washed under nitrogen three times with absolute tetrahydrofuran and subsequently covered with 8 ml. of absolute tetrahydrofuran. thereafter, the mixture is cooled to 0° C. and treated dropwise while stirring with a solution of 2.72 g. of 6-hydroxy-2,3-dihydrobenzofuran in 12 ml. of absolute tetrahydrofuran. The mixture is stirred for 1.5 hours at room temperature and again cooled to 0° C. before a solution of 4.0 g. of 1,3,5-trimethylhexyl p-toluenesulfonate in 10 ml. of absolute tetrahydrofuran is added. Subsequently, the mixture is diluted with 10 ml. of absolute hexamethylphosphoric acid triamide and stirred for 24 hours at room temperature. The mixture is poured onto ice-water and extracted three times with diethyl ether. The extracts are washed with water and saturated aqueous sodium chloride solution, dried over sodium sulfate and evaporated. By chromatography on silica gel with hexane/diethyl ether (98:2 parts by volume) there is obtained pure 6-[(1,3,5-trimethylhexyl)-oxy]-2,3-dihydrobenzofuran which is distilled in a bulb-tube at 118° C./0.3 mmHg; $n_D^{22} = 1.5057$.

EXAMPLE 6

9.4 g. of p-toluenesulfonyl chloride are added with ice cooling to a solution of 6.5 g. of 4,6-dimethyl-2-heptanol in 50 ml. of anhydrous pyridine and the mixture is left for 24 hours at 5° C. Thereafter, the mixture is poured onto ice-water and extracted three times with diethyl ether. The extracts are washed successively with cold 2-N aqueous hydrochloric acid solution, water and twice with saturated sodium chloride solution, dried over sodium sulfate/potassium carbonate and evaporated at room temperature, finally at 0.05 mmHg. There is obtained 1,3,5-trimethylhexyl p-toluenesulfonate which exhibits a spot in the thin-layer chromatogram [$R_f$ = 0.43; hexane/ethyl acetate (9:1 parts by volume)].

EXAMPLE 7

275 mg. of a 55% sodium hydride dispersion in oil are washed under nitrogen three times with absolute tetrahydrofuran and then covered with 5 ml. of absolute tetrahydrofuran. Thereafter, the mixture is cooled to 0° C. and treated dropwise while stirring with a solution of 0.85 g. of 6-hydroxy-2,3-dihydrobenzofuran in 10 ml. of absolute tetrahydrofuran. The mixture is stirred for one hour at room temperature, again cooled to 0° C. and 1.22 g. of 1-bromo-3,7,7-trimethyl-2,4-octadiene dissolved in 10 ml. of absolute tetrahydrofuran are added. Subsequently, the mixture is diluted with 10 ml. of absolute hexamethylphosphoric acid triamide, the ice bath removed and the mixture stirred for 2 hours. Thereafter, the mixture is poured onto ice-water and extracted three times with diethyl ether. The extracts are washed with water and saturated aqueous sodium chloride solution, dried over sodium sulfate and evaporated. By chromatography on silica gel with hexane/diethyl ether (98:2 parts by volume) there is obtained pure 6-[(3,7,7-trimethyl-2,4-octadienyl)-oxy]-2,3-dihydrobenzofuran which is distilled in a bulb-tube at 130° C./0.02 mmHg; $n_D^{20} = 1.5438$.

EXAMPLE 8

23,75 g. of cuprous iodide are placed in a dry reaction vessel and the apparatus is flushed with argon. Then 125 ml. of absolute diethyl ether are added and the suspension is cooled to −40° C. Thereafter, 100 ml. of a 2-M methyl lithium solution in diethyl ether are run in with stirring at −40° C. to −30° C. and a solution of 9.3 g. of 6-methyl-3,5-heptadien-2-one in 75 ml. of absolute diethyl ether is subsequently added in the course of 30 minutes at ca. −30° C. The mixture is allowed to warm to −5° C. with stirring within one hour, then poured onto an ice-cold aqueous ammonium chloride solution, stirred well and filtered through diatomaceous earth. The organic phase is separated and the aqueous phase re-extracted once with diethyl ether. The extracts are washed with saturated sodium chloride solution, dried over sodium sulfate and freed from solvent at 30° C. on a rotary evaporator. The residue is dissolved in 100 ml. of acetone, mixed with 2 ml. of concentrated aqueous hydrochloric acid and left at room temperature for 24 hours. Thereafter, the mixture is poured onto ice-cold 10% by weight aqueous sodium carbonate solution, exhaustively extracted with diethyl ether, the extracts are washed neutral with saturated sodium chloride solution, dried over sodium sulfate and evaporated at 30° C. on a rotary evaporator. By chromatography on silica gel with hexane/diethyl ether (92.5:7.5 parts by volume) there is obtained pure 6,6-dimethyl-3-hepten-2-one which is distilled in a bulb-tube at 60° C./10 mmHg; $n_D^{20} = 1.4460$.

EXAMPLE 9

6.0 g. of 6,6-dimethyl-3-hepten-2-one, 15.0 g. of ethoxycarbonylmethylene-triphenyl-phosphorane and 2.5 g. of benzoic acid are dissolved in 90 ml. of absolute benzene and heated under reflux for 65 hours. The cooled reaction mixture is poured onto 75 ml. of ice-water and 15 ml. of 2-N aqueous sodium hydroxide and the benzene layer separated. The aqueous phase is re-extracted twice with diethyl ether and the extracts are washed with 10% by weight aqueous potassium bicarbonate solution, three times with water and once with saturated sodium chloride solution, dried over sodium sulfate and evaporated. The residue is taken up with a small amount of hexane and filtered. The filtrate is chromatographed on silica gel with hexane-diethyl ether (9:1 parts by volume). 3,7,7-Trimethyl-2,4-octadienoic acid ethyl ester is obtained as an isomer mixture which is distilled in a bulb-tube at 65° C./0.05 mmHg; $n_D^{20} = 1.4855$.

EXAMPLE 10

A solution of 4.2 g. of 3,7,7-trimethyl-2,4-octadienoic acid ethyl ester in 90 ml. of absolute diethyl ether is mixed slowly at −20° C. with stirring and under a nitrogen atmosphere with a suspension of 0.75 g. of lithium aluminum hydride in 45 ml. of absolute diethyl ether. The mixture is allowed to attain room temperature in the course of 2 hours and subsequently decomposed in the cold by the dropwise addition of 60 ml. of 10% by weight aqueous ammonium chloride solution. The resulting mass is vacuum filtered over diatomaceous earth and ethereal phase in the filtrate separated. The aqueous phase is extracted with diethyl ether and the combined ether solutions are washed with saturated sodium chloride solution, dried over sodium sulfate and evaporated. There is obtained 3,7,7-trimethyl-2,4-octadien-1-ol which is purified by distillation. Boiling point (bulb-tube distillation) 60° C./0.03 mmHg; $n_D^{20} = 1.4790$.

EXAMPLE 11

A solution of 1.5 g. of 3,7,7-trimethyl-2,4-octadien-1-ol in 15 ml. of acetyl ether is added dropwise at −20° C. to 1.20 g. of phosphorus tribromide. The temperature is allowed to rise to 0° C. in the course of 30 minutes and then the mixture poured onto 30 ml. of ice-water. The mixture is extracted three times with diethyl ether, the extracts washed with water, 10% by weight aqueous potassium bicarbonate solution and semi-saturated and saturated aqueous sodium chloride solution and then dried over sodium sulfate. After removal of the solvent under reduced pressure in the cold, there is obtained 1-bromo-3,7,7-trimethyl-2,4-octadiene which exhibits a spot in the thin-layer chromatogram [$R_f$ = 0.63; hexane/ethyl acetate (4:1 parts by volume)]. This substance is used in the process without further purification.

EXAMPLE 12

0.875 g. of a 55% by weight sodium hydride dispersion in oil are washed under nitrogen three times with absolute tetrahydrofuran and subsequently covered with 10 ml. of absolute tetrahydrofuran. The mixture is cooled to 0° C. and, in the course of 15 minutes, added dropwise to a solution of 2.27 g. of 6-hydroxy-2,3-dihydrobenzofuran in 12 ml. of absolute tetrahydrofuran. Thereafter, the mixture is stirred for 1 hour at room temperature, again cooling to 0° C. and treated dropwise in the course of 15 minutes with 5.5 g. of 3,7-dimethyl-7-methoxyoctyl p-toluenesulfonate dissolved in 12 ml. of absolute tetrahydrofuran. Subsequently, the mixture is diluted with 12 ml. of absolute hexamethylphosphoric acid triamide, the ice-bath removed and the mixture stirred overnight at room temperature. The mixture is poured onto ice-water and extracted three times with diethyl ether. The extracts are washed with water and twice with saturated sodium chloride solution, dried over sodium sulfate and evaporated. By chromatography on silica gel with hexane/diethyl ether (9:1 parts by volume) there is obtained pure 6-[(3,7-dimethyl-7-methoxy-octyl)-oxy]-2,3-dihydrobenzofuran which is distilled in a bulb-tube at 150° C./0.02 mmHg; $n_D^{20}$ = 1.5086.

EXAMPLE 13

93.2 g. of 7-methoxycitronellal dissolved in 200 ml. of absolute diethyl ether are added dropwise with ice cooling to a suspension of 7.6 g. of lithium aluminum hydride in 500 ml. of absolute diethyl ether. Subsequently, the mixture is stirred for 30 minutes and decomposed in the cold by the addition of 100 ml. of aqueous ammonium chloride solution. The resulting mass is filtered through diatomaceous earth, the filtrate washed once with saturated aqueous ammonium chloride solution and once with saturated aqueous sodium chloride solution, dried over sodium sulfate and evaporated. The residue is distilled at 0.1 mmHg. There is obtained pure 3,7-dimethyl-7-methoxy-1-octanol of boiling point 87° C./0.1 mmHg; $n_D^{20}$ = 1.4456.

EXAMPLE 14

3.76 g. of 3,7-dimethyl-7-methoxy-1-octanol are dissolved in 20 ml. of anhydrous pyridine and mixed, while stirring and with ice cooling, with 4.2 g. of p-toluenesulfochloride. Subsequently, the solution is left overnight at 5° C., then poured onto ice-water and extracted three times with diethyl ether. The extracts are washed successively with cold 2-N aqueous hydrochloric acid solution, water and twice with saturated aqueous sodium chloride solution, dried over sodium sulfate/potassium carbonate and evaporated under reduced pressure, finally at 0.05 mmHg. There is obtained 3,7-dimethyl-7-methoxy-octyl p-toluenesulfonate; $n_D^{20}$ = 1.4927.

EXAMPLE 15

10.9 g. of 6-hydroxy-2,3-dihydrobenzofuran are dissolved in 80 ml. of anhydrous dimethylformamide and treated, while stirring and with ice cooling at 0° C. with 5.3 g. of freshly powdered potassium hydroxide. The mixture is stirred for 1 hour at 0° C. under a nitrogen atmosphere and then added dropwise within 1 hour to a solution of 19.6 g. of 1-bromo-7-ethyl-3-methyl-2,6-nonadiene in 10 ml. of absolute tetrahydrofuran. The mixture is allowed to stir for 2 hours at 0° C. and for 2 hours at room temperature and then poured onto a mixture of 100 ml. of 10% by weight aqueous sodium hydroxide and 100 ml. of ice-water. The mixture is extracted three times with pentane, the extracts are washed successively with 10% by weight aqueous sodium hydroxide, water and saturated sodium chloride solution, dried over sodium sulfate and evaporated. By chromatography on silica gel with hexane/diethyl ether (19:1 parts by volume) there is obtained pure 6-[(7-ethyl-3-methyl-2,6-nonadienyl)-oxy]-2,3-dihydrobenzofuran which is distilled in a bulb-tube at 132° C./0.02 mmHg; $n_D^{20}$ = 1.5350.

EXAMPLE 16

18.2 g. of 7-ethyl-3-methyl-1,6-nonadien-3-ol, 100 ml. of hexane and 1 ml. of anhydrous pyridine are cooled to −15° C. and treated dropwise in the course of 1.5 hours with a solution of 4 ml. of phosphorus tribromide in 50 ml. of hexane, the temperature being maintained at between −15° C. and −10° C. The mixture is stirred for a further 1.5 hours during which time it is allowed to warm up to room temperature slowly. For working up, the mixture is poured onto 50 ml. of ice-water, the organic phase separated and washed in turn with 20 ml. of 10% by weight aqueous sodium carbonate solution, 50 ml. of semi-saturated aqueous sodium chloride solution and 50 ml. of saturated aqueous sodium chloride solution, dried over sodium sulfate and evaporated under reduced pressure. There is obtained 1-bromo-7-ethyl-3-methyl-2,6-nonadiene which is used in the process without further purification.

EXAMPLE 17

A solution of 2.7 g. of 6-hydroxy-2,3-dihydrobenzofuran in 10 ml. of absolute tetrahydrofuran is allowed to drop at 0° C. and while stirring into a suspension, cooled in ice, of 0.5 g. of sodium hydride in 5 ml. of absolute tetrahydrofuran. The mixture is stirred for 2 hours (during which time it is allowed to warm up to room temperature), again cooled to 0° C. and added dropwise to a solution of 7.13 g. of 7-methoxy-1,3,7-trimethyloctyl p-toluenesulfonate in 10 ml. of absolute tetrahydrofuran. The mixture is then diluted with 4 ml. of absolute hexamethylphosphoric acid triamide and stirred for 20 hours at room temperature. The mixture is then poured onto ice-water, extracted three times with diethyl ether, the ether extracts are washed with water and saturated aqueous sodium chloride solution, dried over sodium sulfate and evaporated. By chromatography on silica gel with hexane/ethyl acetate (19:1 parts by volume) there is obtained pure 2,3-dihydro-6-[(7-methoxy-1,3,7-trimethyloctyl)-oxy]-benzofuran which is distilled in a bulb-tube at 145° C./0.03 mmHg; $n_D^{20}$ = 1.5046.

EXAMPLE 18

A solution of 28 g. of methoxycitronellal in 50 ml. of ether is slowly added dropwise at −20° C. to −10° C. to a Grignard solution prepared from 5.35 g. of magnesium and 28.4 g. of methyl iodide in 100 ml. of diethyl ether. The mixture is then poured onto 100 ml. of ice-water, acidified with dilute aqueous sulfuric acid and extracted twice with diethyl ether. The extracts are washed with semi-saturated and saturated sodium chloride solution, dried over sodium sulfate and evaporated. By distillation in a high vacuum there is obtained pure 8-methoxy-4,8-dimethyl-2-nonanol of boiling point 103° C./0.8 mmHg; $n_D^{20} = 1.4451$.

EXAMPLE 19

10.1 g. of 8-methoxy-4,8-dimethyl-2-nonanol are dissolved in 50 ml. of pyridine and treated portionwise with ice cooling and stirring with 10.45 g. of pure toluene-4-sulfochloride. After standing for 2 days at ca. 5° C., the mixture is poured onto ice-water and acidified with half-concentrated aqueous hydrochloric acid. The mixture is then extracted three times with diethyl ether, the extracts are washed with semi-saturated and saturated aqueous sodium chloride solution, dried over sodium sulfate/potassium carbonate and the solvent is removed under reduced pressure, finally in a high vacuum. There is obtained 7-methoxy-1,3,7-trimethyloctyl p-toluenesulfonate; $n_D^{20} = 1.4890$.

EXAMPLE 20

By the procedure of Example 17:
3,7-dimethyl-6-octenyl p-toluenesulfonate and 6-hydroxy-2,3-dihydrobenzofuran are reacted to produce 6-[(3,7-dimethyl-6-octenyl)-oxy]-2,3-dihydrobenzofuran of boiling point 126°–128° C./0.001 mmHg; $n_D^{20} = 1.5223$; and 3,7-dimethyl-6-octenyl p-toluenesulfonate and 6-hydroxy-3-methyl-2,3-dihydrobenzofuran are reacted to produce 6-[(3,7-dimethyl-6-octenyl)-oxy]-3-methyl-2,3-dihydrobenzofuran of boiling point (bulb-tube) 130° C./0.14 mmHg; $n_D^{20} = 1.5150$.

The starting material 3,7-dimethyl-6-octenyl p-toluenesulfonate ($n_D^{21} = 1.5022$) is obtained from citronellol by the procedure given in Examples 18 and 19.

EXAMPLE 21

1.0 g. of 6-[(6,7-epoxy-3,7-dimethyl-2-nonenyl)-oxy]-2,3-dihydrobenzofuran is dissolved in 25 ml. of ethyl acetate and hydrogenated in the presence of 50 mg. of platinum oxide until the theoretical amount of hydrogen has been taken up. The catalyst is then removed by filtration and the filtrate evaporated. By chromatography on silica gel using hexane/diethyl ether (19:1 parts by volume) there is obtained pure 6-[(6,7-epoxy-3,7-dimethylnonyl)-oxy]-2,3-dihydrobenzofuran; $n_D^{20} = 1.5118$.

EXAMPLE 22

By the procedure of Example 21:
6-[(6,7-epoxy-3,7,9-trimethyl-2-decenyl)-oxy]-2,3-dihydrobenzofuran is converted to 6-[(6,7-epoxy-3,7,9-trimethyldecyl)-oxy]-2,3-dihydrobenzofuran of boiling point (bulb-tube) 140° C./0.03 mmHg; $n_D^{23} = 1.5083$;

6-[(6,7-epoxy-3,7-dimethyl-2-nonenyl)-oxy]-3-methyl-2,3-dihydrobenzofuran is converted to 6-[(6,7-epoxy-3,7-dimethylnonyl)-oxy]-3-methyl-2,3-dihydrobenzofuran of boiling point ca. 165° C./0.001 mmHg; $n_D^{20} = 1.5108$; and 6-[3,7-dimethyl-6-octenyl)-oxy]-2,3-dihydrobenzofuran is converted to 6-[(3,7-dimethyloctyl)-oxy]-2,3-dihydrobenzofuran of boiling point 116°–117° C./0.001 mmHg; $n_D^{20} = 1.5102$.

EXAMPLE 23

A solution of 3.48 g. of 6-[(3,7-dimethyl-6-octenyl)-oxy]-3-methyl-2,3-dihydrobenzofuran in 15 ml. of absolute ethyl alcohol is slowly added dropwise at room temperature to a suspension of 3.81 g. of mercuric acetate in 30 ml. of absolute ethyl alcohol. The mixture is thereupon stirred for one hour at room temperature, cooled by means of an ice bath and 12.8 ml. of 10% by weight aqueous hydroxide followed by 0.24 g. of sodium borohydride in 12.8 ml. of 10% by weight aqueous sodium hydroxide are added dropwise. After stirring for 30 minutes at room temperature, the mixture is filtered through diatomaceous earth, the aqueous phase saturated with sodium chloride and subsequently extracted with pentane. The extracts are washed neutral with aqueous sodium chloride solution, dried over sodium sulfate and evaporated. By chromatography on silica gel there is obtained pure 6-[(7-ethoxy-3,7-dimethyl-octyl)-oxy]-3-methyl-2,3-dihydrobenzofuran which is distilled in a bulb-tube at 132° C./0.01 mmHg; $n_D^{22} = 1.4976$.

EXAMPLE 24

By the procedure of Example 23:
6-[(3,7-dimethyl-6-octenyl)-oxy]-2,3-dihydrobenzofuran is converted to 6-[(7-ethoxy-3,7-dimethyloctyl)-oxy]-2,3-dihydrobenzofuran of boiling point (bulb-tube) 132° C./0.01 mmHg; $n_D^{22} = 1.5018$.

EXAMPLE 25

875 mg. of a 55% by weight sodium hydride dispersion in oil are washed three times with absolute tetrahydrofuran and then covered with 10 ml. of absolute tetrahydrofuran. Thereafter, the mixture is treated at 0° C. and while stirring with a solution of 2.72 g. of 6-hydroxy-2,3-dihydrobenzofuran in 12 ml. of absolute tetrahydrofuran. The mixture is stirred for one hour (during which time it is allowed to warm up to room temperature), then again cooled to 0° C. and added dropwise to a solution of 1-bromo-7-ethoxy-3,7-dimethyl-2-octene in 12 ml. of absolute tetrahydrofuran. 12 ml. of pure hexamethylphosphoric acid triamide are then added to the mixture, the ice bath is removed and the mixture stirred for 3 hours. The mixture is worked up by pouring it onto ice-water and extracting the resulting mixture three times with diethyl ether. The extracts are washed with water and saturated aqueous sodium chloride solution, dried over sodium sulfate and evaporated. By chromatography on silica gel with hexane/diethyl ether (19:1 parts by volume) there is obtained pure 6-[(7-ethoxy-3,7-dimethyl-2-octenyl)-oxy]-2,3-dihydrobenzofuran which is distilled in a bulb-tube at 150° C./0.05 mmHg; $n_D^{20.5} = 1.5172$.

EXAMPLE 26

50 ml. of concentrated sulfuric acid are slowly added dropwise at −5° C. to 0° C. to 460 ml. of absolute ethyl aclohol. The solution is then treated, while slowly warming to 20° C., with 126 g. of methylheptenone. The mixture is stirred for 24 hours at room temperature, then poured into 750 ml. of water and the oily layer separated off. The aqueous phase is extracted four times with 75 ml. of benzene each time and the extracts are combined with the oily layer. The combined solutions are washed twice with water and twice with saturated aqueous sodium chloride solution, dried over sodium sulfate and freed from the solvent under reduced pressure. By distillation there is obtained pure 6-ethoxy-6-methyl-2-heptanone of boiling point 86°–88° C./10 mmHg; $n_D^{24} = 1.4287$.

EXAMPLE 27

16.4 g. of a 55% sodium hydride dispersion in oil are washed three times with hexane and then covered with 200 ml. of dimethylformamide. A solution of 84 g. of diethylphosphonoacetic acid ethyl ester in 400 ml. of dimethylformamide is then added dropwise under a nitrogen atmosphere in the course of 2.5 hours, the temperature increasing slightly during this addition. After completion of the addition, the mixture is stirred for a further 1 hour at room temperature and then treated slowly with a solution of 43 g. of 6-ethoxy-6-methyl-2-heptanone in 400 ml. of dimethylformamide. The mixture is then left to stand overnight at room temperature and is subsequently stirred for a further 5 hours at 55° C. The mixture is poured onto 250 ml. of ice-water and extracted three times with diethyl ether. The extracts are washed twice with water and once with saturated sodium chloride solution, dried over sodium sulfate and evaporated under reduced pressure. By distillation there is obtained pure 7-ethoxy-3,7-dimethyl-2-octenoic acid ethyl ester of boiling point 83°–85° C./0.03 mmHg; $n_D^{24} = 1.4572$.

EXAMPLE 28

7-Ethoxy-3,7-dimethyl-2-octen-1-ol (boiling point 77°–78° C./0.02 mmHg; $n_D^{24} = 1.4584$) is obtained from 7-ethoxy-3,7-dimethyl-2-octenoic acid ethyl ester by treatment with lithium aluminum hydride by the procedure described in Example 10.

1-Bromo-7-ethoxy-3,7-dimethyl-2-octene ($n_D^{20} = 1.4862$) is obtained from 7-ethoxy-3,7-dimethyl-2-octen-1-ol by treatment with phosphorus tribromide by the procedure described in Example 11.

EXAMPLE 29

By the procedure described in Example 17:

1,5-dimethyl-4-heptenyl p-toluenesulfonate and 6-hydroxy-2,3-dihydrobenzofuran are reacted to produce 6-[(1,5-dimethyl-4-heptenyl)-oxy]-2,3-dihydrobenzofuran of boiling point (bulb-tube) 120° C./0.02 mmHg; $n_D^{20} = 1.5226$; and 5-ethoxy-1,5-dimethylhexyl p-toluenesulfonate and 6-hydroxy-2,3-dihydrobenzofuran are reacted to produce 6-[(5-ethoxy-1,5-dimethylhexyl)-oxy]-2,3-dihydrobenzofuran of boiling point (bulb-tube) 127° C./0.02 mmHg; $n_D^{24} = 1.5023$.

EXAMPLE 30

A solution of 43 g. of 6-ethoxy-6-methyl-2-heptanone in 100 ml. of absolute diethyl ether is slowly added dropwise with ice cooling to a suspension of 4.5 g. of lithium aluminum hydride in 400 ml. of absolute diethyl ether. The mixture is subsequently stirred for a further one hour at ca. 5° C. and then hydrolyzed by the cautious addition of a dilute aqueous ammonium chloride solution. The mixture is filtered through diatomaceous earth and the organic phase washed with saturated sodium chloride solution, dried over sodium sulfate and evaporated under reduced pressure. By distillation there is obtained pure 6-ethoxy-6-methyl-2-heptanol of boiling point 100° C./10 mmHg; $n_D^{20} = 1.4372$.

5-Ethoxy-1,5-dimethylhexyl p-toluenesulfonate ($n_D^{20} = 1.4898$) is obtained from 6-ethoxy-6-methyl-2-heptanol by the procedure described in Example 19.

EXAMPLE 31

An ice-cold solution of 6.0 g. of 6-[(3,7-dimethyl-2,6-nonadienyl)-oxy]-2,3-dihydrobenzofuran in 40 ml. of absolute methanol is treated dropwise while stirring with a solution of 6.7 g. of mercuric acetate in 100 ml. of methanol. The mixture is stirred for 2 hours at room temperature, after which there are added in the cold 23 ml. of 10% by weight aqueous sodium hydroxide followed by 0.4 g. of sodium borohydride in 23 ml. of 10% by weight aqueous sodium hydroxide. The mixture is stirred for 20 minutes at room temperature, filtered through diatomaceous earth, the filtrate saturated with sodium chloride and extracted three times with diethyl ether. The extracts are washed neutral with sodium chloride solution, dried over sodium sulfate and evaporated. By chromatography on silica gel with hexane/ethyl acetate (19:1 parts by volume) there is obtained pure 2,3-dihydro-6-[(7-methoxy-3,7-dimethyl-2-nonenyl)-oxy]-benzofuran which is distilled in a bulb-tube at 125° C./0.03 mmHg; $n_D^{20} = 1.5236$.

EXAMPLE 32

By the procedure of Example 31:
2,3-dihydro-6-[(1,5-dimethyl-4-heptenyl)-oxy]-benzofuran is converted to 2,3-dihydro-6-[(5-methoxy-1,5-dimethylheptyl)-oxy]-benzofuran of boiling point (bulb-tube) 130° C./0.03 mmHg; $n_D^{20} = 1.5103$.

EXAMPLE 33

By the procedure described in Example 17, there is obtained from 1,3,5,5-tetramethylhexyl p-toluenesulfonate and 6-hydroxy-2,3-dihydrobenzofuran, the compound 6-[(1,3,5,5-tetramethylhexyl)-oxy]-2,3-dihydrobenzofuran of boiling point (bulb-tube) 110° C./0.04 mmHg; $n_D^{20} = 1.5020$.

EXAMPLE 34

250 ml. of a ca. 2-M ethereal methyl lithium solution are added dropwise to 39.5 g. of 3,5,5-trimethylhexanoic acid in 250 ml. of absolute diethyl ether at such a rate that a slight reflux is maintained. After completion of the addition, the mixture is stirred at room temperature for 1.5 hours, then cooled in an ice bath and 100 ml. of saturated aqueous ammonium chloride solution are cautiously added dropwise with stirring. The mixture is filtered through diatomaceous earth and the two phases of the filtrate are separated. The aqueous phase is back-extracted once with diethyl ether and the ether solutions are washed successively with ammonium chloride solution, water and saturated aqueous sodium chloride solution, dried over sodium sulfate and evaporated. By distillation there is obtained pure 4,6,6-trimethyl-2-heptanone of boiling point 64°–67° C./12 mmHg; $n_D^{20} = 1.4258$.

Pure 4,6,6-trimethyl-2-heptanol (boiling point: 76° C./13 mm; $n_D^{22} = 1.4318$) is obtained from 4,6,6-trimethyl-2-heptanone by treatment with lithium aluminum hydride by the procedure described in Example 30.

1,3,5,5-Tetramethylhexyl p-toluenesulfonate ($n_D^{23}$ = 1.4880) is obtained from 4,6,6-trimethyl-2-heptanol by the procedure described in Example 19.

EXAMPLE 35

0.4 g. of 6-[(6-hydroxy-3,7,7-trimethyl-2-octenyl)-oxy]-2,3-dihydrobenzofuran are dissolved in 10 ml. of absolute tetrahydrofuran and, while stirring, warmed to 40° C. for 2 hours with 0.5 g. of a 55% by weight sodium hydride suspension in oil. Then 2 ml. of hexamethylphosphoric acid triamide and 1 ml. of methyl iodide are added and the mixture is stirred for 12 hours at room temperature. For the working up, the mixture is poured onto ice-water and extracted twice with diethyl ether. The ether extracts are washed with water and saturated aqueous sodium chloride solution, dried over sodium sulfate and evaporated. By chromatography on silica gel with hexane/diethyl ether (19:1 parts by volume) there is obtained 6-[(6-methoxy-3,7,7-trimethyl-2-octenyl)-oxy]-2,3-dihydrobenzofuran; $n_D^{25}$ = 1.5170.

EXAMPLE 36

4.64 g. of 6-[(6,7-epoxy-3,7-dimethyl-2,6-nonadienyl)-oxy]-2,3-dihydrobenzofuran (see Example 3) are dissolved in 14 ml. of tetrahydrofuran, diluted with 7.5 ml. of water and treated with a mixture of 0.1 ml. of 70% by weight perchloric acid in 1 ml. of water. The mixture is stirred at room temperature for 4 hours, 10 ml. of saturated aqueous sodium chloride solution are added thereto and the resulting mixture is extracted three times with diethyl ether methylene chloride (9:1 parts by volume). The extracts are washed with saturated sodium chloride solution, dried over sodium sulfate and evaporated. The thus-obtained crude diol is dissolved in 30 ml. of tetrahydrofuran and treated, with ice cooling and under a nitrogen atmosphere, with a solution of 3.2 g. of sodium metaperiodate in 35 ml. of water following which the mixture is stirred overnight at room temperature. For working up, 100 ml. of water are added to the mixture which is then extracted three times with diethyl ether. The extracts are washed with 10% by weight aqueous potassium bicarbonate solution and with semi-saturated and saturated sodium chloride solution, dried over sodium sulfate and evaporated. By chromatography on silica gel with hexane/ethyl acetate (19:1 parts by volume) there is obtained pure 6-[(6-oxo-3-methyl-2-hexenyl)-oxy]-2,3-dihydrobenzofuran which is distilled in a bulb-tube at 100° C./0.02 mmHg.

EXAMPLE 37

1.94 g. of 6-[(6-oxo-3-methyl-2-hexenyl)-oxy]-2,3-dihydrobenzofuran are dissolved in 80 ml. of absolute diethyl ether and treated dropwise at 0° C. under nitrogen over a period of 20 minutes with 5 ml. of a 2-M solution of tertbutyl lithium in pentane. The mixture is then poured into ice-cold saturated aqueous ammonium chloride solution and extracted twice with diethyl ether. The extracts are dried over sodium sulfate and evaporated. There is obtained crude 6-[(6-hydroxy-3,7,7-trimethyl-2-octenyl)-oxy]-2,3-dihydrobenzofuran which is used in the process without further purification.

EXAMPLES 38–40

The Examples 38–40 illustrate the efficacy of the phenyl derivatives provided by the present invention. In these Examples, the term "active substance" means a phenyl derivative of formula I hereinbefore.

EXAMPLE 38

20 Mature rice flour beetles (Tribolium castaneum) are brought into contact in plastic cages for 5 days with wheat flour. This wheat flour is impregnated with a solution in acetone of $10^{-x}$ g. of active substance per gram of wheat meal. After 5 days, the beetles are removed and the plastic cages are maintained at 29° C. and 75–80% relative humidity until the $F_1$ generation has hatched. Analogous experiments with untreated wheat meal and with wheat meal treated with acetone alone serve as the controls. The results are expressed in the percentage reduction of the $F_1$ generation in comparison with the controls. The calculation is carried out according to the following equation:

$$\% \text{ Reduction} = \frac{F_1 \text{ generation } (\overline{AC} + \overline{UC}) - F_1 \text{ generation (treated)}}{F_1 \text{ generation } (AC + UC)} \times 100$$

$\overline{AC}$ = Mean value from control experiments with wheat meal treated with acetone.

$\overline{UC}$ = Mean value from control experiments with untreated wheat meal.

| Active substance | Dosage $10^{-x}$ | % Reduction of the $F_1$ generation |
|---|---|---|
| 6-[(7-ethoxy-3,7-dimethyl-2-octenyl)-oxy]-2,3-dihydrobenzofuran | 4 | 100 |
| | 5 | 100 |
| | 6 | 97 |
| | 7 | 41 |
| | 8 | 16 |

EXAMPLE 39

The following example illustrates the high stability of the phenyl derivatives provided by the invention in comparison with known compounds in "pukka" water ("pukka" water is water standardized to the World Health Organization specification) and in distilled water. For this purpose, 10 mg. of active substance are introduced into 1000 ml. of pukka water or distilled water. After 3 days, 1, 2, 3 and 4 weeks, samples are taken and these samples are treated with an internal standard. The internal standard is always chosen so as to guarantee as close a possible relationship between the physical properties of the standard and those of the active substances under investigation. 6,7-Epoxy-3,7-dimethyl-1-(p-ethylphenoxy)-octane is used as the internal standard for the compounds listed in the following Table. The samples are extracted with dichloromethane, the extracts are evaporated and the percentage content of active substance in the residue is determined with a capillary chromatograph, which is provided with an automatic digital integrator, by comparison with the internal standard (present in a known concentration). The following Table gives data obtained in a typical experiment carried out as described earlier:

| Active Substance | 10 mg. in 1 liter of "pukka" water. Content in % after weeks | | | | 10 mg. in 1 liter of distilled water. Content in % water | | |
|---|---|---|---|---|---|---|---|
| | 1 | 2 | 3 | 4 | 3 days | 1 week | 2 weeks |
| 6-[(6,7-epoxy-3,7-dimethyl-2-nonenyl)-oxy]-2,3-dihydrobenzofuran | 25 | 17 | 5 | 0 | — | — | — |
| 6-[(6,7-epoxy-3,7-dimethyl-2-octenyl)-oxy]-2,3-dihydrobenzofuran | — | — | — | — | 41 | 15 | 25 |

EXAMPLE 40

The following example illustrates the slight phytotoxicity of the phenyl derivatives provided by the invention in comparison with known compounds. For this purpose, cotton plants and tomato plants are sprayed by means of a spray-pistol with a solution containing 0.4% by weight of active substance until the solution drips off the plants. After spraying, the plants are incubated in a climatic cabin at 25° C. and 70% relative humidity. After 48 hours, the scorchings and necroses appearing on the foilage of the plants are evaluated, the percentage destruction or affected foilage mass being given relative to the total foilage mass. Control experiments are carried out at the same time without using the active substance. The 0.4% by weight solution of the active substance is prepared by diluting a concentrate with the requisite amount of water. The concentrate has the following composition:

| Emulphor El 620 | 12% |
|---|---|
| Drewmulse | 13% |
| Uvinul M-539 | 5% |
| Drew oil 1400 | 20% |
| Active substance | 50% |

The following Table gives the percent destruction as described above:

| Active Substance | Scorchings in necroses | |
|---|---|---|
| | Cotton Plants | Tomato plants |
| 6-[(6,7-epoxy-3,7-dimethyl-2-nonenyl)-oxy]-2,3-dihydrobenzofuran | 0 | 1 |
| 6-[(6,7-epoxy-3-ethyl-7-methyl-2-nonenyl)-oxy]-2,3-dihydrobenzofuran | 0 | 0 |

We claim:
1. A compound of the formula

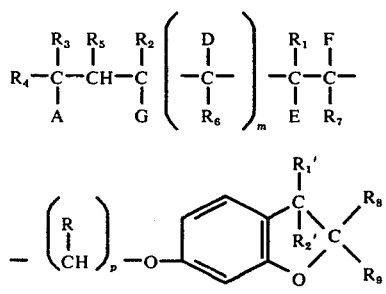

wherein R, $R_1$, $R_2$, $R_3$, $R_4$, $R_5$, $R_6$, $R_7$, $R_8$, $R_9$, $R_1'$ and $r_2'$ are hydrogen or lower alkyl; A is hydrogen, lower alkyl, lower alkoxy, lower alkenyloxy, or lower alkynyloxy; G and D are individually hydrogen or taken together form a carbon to carbon bond; E and F are individually hydrogen or taken together form a carbon to carbon bond; $m$ is an integer of from 0 to 1; and $p$ is an integer from 1 to 2.

2. The compound of claim 1 wherein A is hydrogen.
3. The compound of claim 1 wherein A is lower alkoxy.
4. The compound of claim 1 wherein A is lower alkynyloxy.
5. The compound of claim 1 wherein A is lower alkyl.
6. The compound of claim 4 wherein $R_1'$, $R_2'$, $R_8$ and $R_9$ are hydrogen.
7. The compound of claim 6 wherein said compound is 6-[(1,3,5-trimethylhexyl)-oxy]-2,3-dihydrobenzofuran.
8. The compound of claim 7 wherein said compound is 6-[(3,7-dimethyloctyl)-oxy]-2,3-dihydrobenzofuran.
9. The compound of claim 4 wherein at least one of $R_8$ and $R_9$ is lower alkyl.
10. The compound of claim 9 wherein said compound is 6-[(3,7-dimethyl-2-octenyl)-oxy]-2,2-dimethyl-2,3-dihydrobenzofuran.
11. The compound of claim 9 wherein said compound is 6-[(3,7-dimethyl-2-octenyl)-oxy]-2-methyl-2,3-dihydrobenzofuran.
12. The compound of claim 4 wherein at least one of $R_1'$ and $R_2'$ is lower alkyl.
13. The compound of claim 12 wherein said compound is 6-[(3,7-dimethyl-2-octenyl)-oxy]-3-methyl-2,3-dihydrobenzofuran.
14. The compound of claim 12 wherein said compound is 6-[(3,7-dimethyl-2-octenyl)-oxy]-3,3-dimethyl-2,3-dihydrobenzofuran.
15. The compound of claim 5 wherein $R_1'$, $R_2'$, $R_8$ and $R_9$ are hydrogen.
16. The compound of claim 15 wherein said compound is 6-[(7-ethoxy-3,7-dimethyloctyl)-oxy]-2,3-dihydrobenzofuran.
17. The compound of claim 15 wherein said compound is 6-[(7-ethoxy-3,7-dimethyl-2-octenyl)-oxy]-2,3-dihydrobenzofuran.

18. The compound of claim 15 wherein said compound is 6-[(5-ethoxy-1,5-dimethylhexyl)-oxy]-2,3-dihydrobenzofuran.

19. The compound of claim 5 wherein at least one of $R_8$ and $R_9$ is lower alkyl.

20. The compound of claim 19 wherein said compound is 6-[(7-methoxy-3,7-dimethyloctyl)-oxy]-2-methyl-2,3-dihydrobenzofuran.

21. The compound of claim 19 wherein said compound is 6-[(5-methoxy-1,5-dimethylheptyl)-oxy]-2,2-dimethyl-2,3-dihydrobenzofuran.

22. The compound of claim 5 wherein at least one of $R_8$ and $R_9$ is lower alkyl.

23. The compound of claim 22 wherein said compound is 6-[(5-methoxy-1,5-dimethylheptyl)-oxy]-3-methyl-2,3-dihydrobenzofuran.

24. The compound of claim 23 wherein said compound is 6-[(7-methoxy-3,7-dimethylnonyl)-oxy]-3,3-dimethyl-2,3-dihydrobenzofuran.

25. The compound of claim 24 wherein $R_1'$, $R_2'$, $R_8$ and $R_9$ are hydrogen.

26. The compound of claim 25 wherein said compound is 6-[(3,7-dimethyl-7-(2-propynyloxy)-2-octenyl)-oxy]-2,3-dihydrobenzofuran.

27. The compound of claim 25 wherein at least one of $R_8$ and $R_9$ is lower alkyl.

28. The compound of claim 27 wherein said compound is 6-[(3,7-dimethyl-7-(2-propynyloxy)-2-octenyl)-oxy]-2-methyl-2,3-dihydrobenzofuran.

29. The compound of claim 27 wherein said compound is 6-[(3,7-dimethyl-7-(2-propynyloxy)-2-octenyl)-oxy]-2,2-dimethyl-2,3-dihydrobenzofuran.

30. The compound of claim 24 wherein at least one of $R_1'$ and $R_2'$ are lower alkyl.

31. The compound of claim 30 wherein said compound is 6-[(3,7-dimethyl-7-(2-propynyloxy)-2-octenyl)-oxy]-3-methyl-2,3-dihydrobenzofuran.

32. The compound of claim 30 wherein said compound is 6-[(3,7-dimethyl-7-(2-propynyloxy)-octyl)-oxy]-3-methyl-2,3-dihydrobenzofuran.

33. The compound of claim 31 wherein $R_1'$, $R_2'$, $R_7$ and $R_8$ are hydrogen.

34. The compound of claim 33 wherein said compound is 6-[(3,7,7-trimethyl-2-octenyl)-oxy]-2,3-dihydrobenzofuran.

35. The compound of claim 33 wherein said compound is 6-[(3,7,7-trimethyl-2,4-octadienyl)-oxy]-2,3-dihydrobenzofuran.

36. The compound of claim 31 wherein at least one of $R_8$ and $R_9$ are lower alkyl.

37. The compound of claim 36 wherein said compound is 6-[(3,7,7-tri-methyl-2-octenyl)-oxy]-2-methyl-2,3-dihydrobenzofuran.

38. The compound of claim 36 wherein the compound is 6-[(3,7,7-trimethyl-2-octenyl)-oxy]-2,2-dimethyl-2,3-dihydrobenzofuran.

39. The compound of claim 1 wherein at least one of $R_1'$ and $R_2'$ are lower alkyl.

40. The compound of claim 39 wherein said compound is 6-[(3,7,7-trimethyl-2-octenyl)-oxy]-3-methyl-2,3-dihydrobenzofuran.

41. The compound of claim 39 wherein said compound is 6-[(3,7,7-trimethyl-2-octenyl)-oxy]-3,3-dimethyl-2,3-dihydrobenzofuran.

* * * * *